US010857358B2

(12) United States Patent
Bouton et al.

(10) Patent No.: US 10,857,358 B2
(45) Date of Patent: Dec. 8, 2020

(54) SYSTEMS FOR NEURAL BRIDGING OF THE NERVOUS SYSTEM

(71) Applicant: Battelle Memorial Institute, Columbus, OH (US)

(72) Inventors: Chad E. Bouton, Columbus, OH (US); Nicholas Annetta, Columbus, OH (US); David A. Friedenberg, Columbus, OH (US); Gaurav Sharma, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 198 days.

(21) Appl. No.: 15/578,776

(22) PCT Filed: Jun. 2, 2016

(86) PCT No.: PCT/US2016/035524
§ 371 (c)(1),
(2) Date: Dec. 1, 2017

(87) PCT Pub. No.: WO2016/196797
PCT Pub. Date: Dec. 8, 2016

(65) Prior Publication Data
US 2018/0178008 A1     Jun. 28, 2018

Related U.S. Application Data

(60) Provisional application No. 62/169,820, filed on Jun. 2, 2015.

(51) Int. Cl.
*A61B 5/00*     (2006.01)
*A61N 1/36*     (2006.01)
(Continued)

(52) U.S. Cl.
CPC ........ *A61N 1/36003* (2013.01); *A61B 5/0482* (2013.01); *A61B 5/1124* (2013.01);
(Continued)

(58) Field of Classification Search
CPC ..... A61B 2505/09; A61B 5/0482; A61B 5/11; A61B 5/1124; A61B 5/16; A61B 5/165;
(Continued)

(56) References Cited

U.S. PATENT DOCUMENTS 7,164,967 B2    1/2007  Etienne-Cummings et al.
2005/0182457 A1  8/2005  Thrope et al.
(Continued)

FOREIGN PATENT DOCUMENTS

EP    0103491 A1    3/1984

OTHER PUBLICATIONS

International Search Report and Written Opinion dated Aug. 10, 2016 in PCT/US2016/035524.

*Primary Examiner* — George Manuel
(74) *Attorney, Agent, or Firm* — Fay Sharpe LLP

(57) ABSTRACT

The present disclosure relates generally to systems, methods, and devices for interpreting neural signals to determine a desired movement of a target, transmitting electrical signals to the target, and dynamically monitoring subsequent neural signals or movement of the target to change the signal being delivered if necessary, so that the desired movement is achieved. In particular, the neural signals are decoded using a feature extractor, decoder(s) and a body state observer to determine the electrical signals that should be sent.

19 Claims, 19 Drawing Sheets

(51) Int. Cl.
- *A61B 5/0482* (2006.01)
- *A61B 5/11* (2006.01)
- *A61N 1/05* (2006.01)
- *A61F 2/72* (2006.01)
- *A61F 4/00* (2006.01)
- *A61G 5/00* (2006.01)
- *A61H 3/00* (2006.01)
- *A61B 5/16* (2006.01)

(52) U.S. Cl.
CPC .......... *A61B 5/4836* (2013.01); *A61B 5/7203* (2013.01); *A61F 2/72* (2013.01); *A61F 4/00* (2013.01); *A61G 5/00* (2013.01); *A61H 3/00* (2013.01); *A61N 1/0551* (2013.01); *A61B 5/11* (2013.01); *A61B 5/165* (2013.01); *A61B 5/168* (2013.01); *A61B 5/686* (2013.01); *A61B 2505/09* (2013.01)

(58) Field of Classification Search
CPC ....... A61B 5/168; A61B 5/4836; A61B 5/686; A61B 5/7203; A61F 2/72; A61F 4/00; A61G 5/00; A61H 3/00; A61N 1/0551; A61N 1/36003

See application file for complete search history.

(56) References Cited

U.S. PATENT DOCUMENTS

| | | |
|---|---|---|
| 2009/0082829 A1 | 3/2009 | Panken et al. |
| 2010/0286748 A1 | 11/2010 | Midani et al. |
| 2011/0098783 A1 | 4/2011 | Schuler |
| 2012/0123293 A1 | 5/2012 | Shah et al. |
| 2013/0123568 A1 | 5/2013 | Hamilton et al. |
| 2013/0253299 A1 | 9/2013 | Weber et al. |
| 2014/0089266 A1 | 3/2014 | Une et al. |
| 2014/0288667 A1 | 9/2014 | Oxley |
| 2014/0358192 A1 | 12/2014 | Wheeler Moss et al. |
| 2016/0271395 A1* | 9/2016 | Kramer ................ A61N 1/0551 |

* cited by examiner

Hand pronation, palm down

Perpendicular arm lift

Hand neutral position

Hand pronation, thumb down

Supination, palm up
 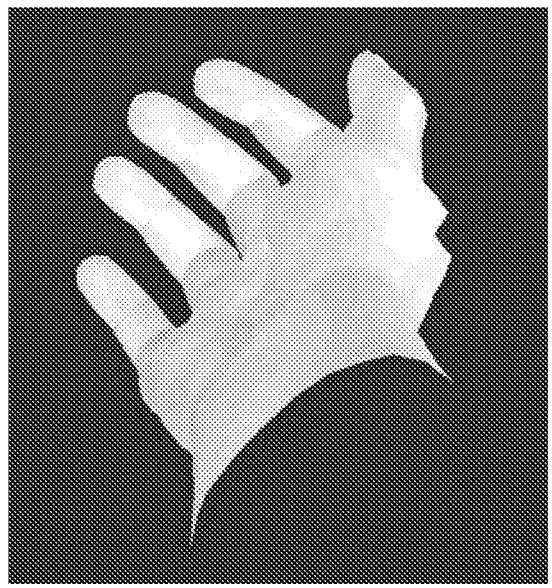
FIG. 11A  FIG. 11B
Wrist extension
 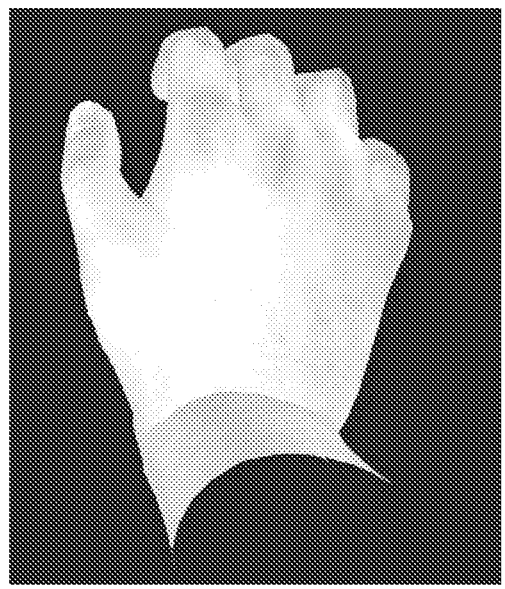
FIG. 12A  FIG. 12B Wrist flexion
 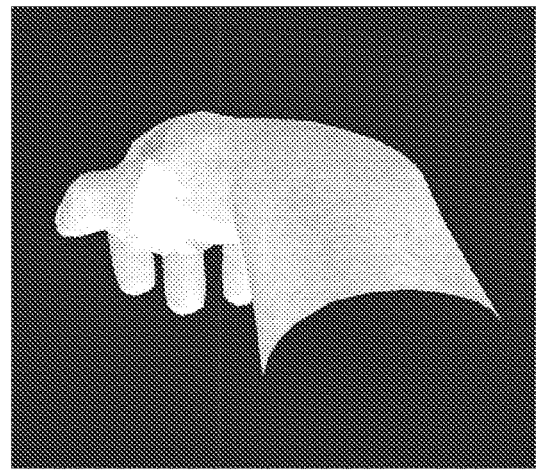
FIG. 13A   FIG. 13B
Radial deviation
 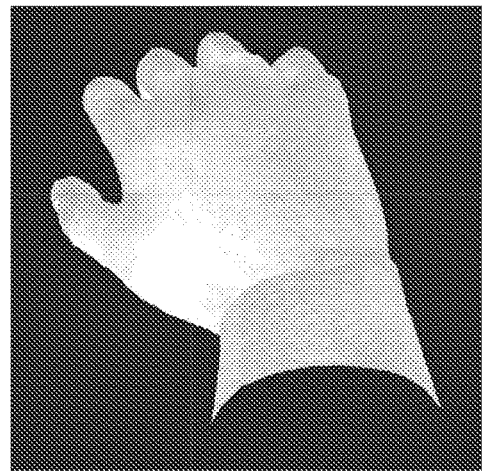
FIG. 14A   FIG. 14B Ulnar deviation Finger extension Finger fair curvature Fist Finger extension Finger fair curvature Fist

SYSTEMS FOR NEURAL BRIDGING OF THE NERVOUS SYSTEM

CROSS-REFERENCE TO RELATED APPLICATIONS

This application is a 371 of PCT Patent Application Serial No. PCT/US2016/035524, filed Jun. 2, 2016, which claims priority to U.S. Provisional Patent Application Ser. No. 62/169,820, filed Jun. 2, 2015.

BACKGROUND

The present disclosure relates generally to systems, methods and devices for neuromuscular stimulation by interpretation of neural activity and processing to identify desired movements of a target, and provide appropriate stimulation to the target to cause the desired movements.

Many millions of people suffer from some motor impairment. For example, it is estimated that worldwide, 10 million people are left disabled following a stroke each year. People also suffer from brain injury, failed back surgery or spinal cord injury. These injuries can result in motor impairment by damaging the link between the brain and the muscles of the body which are used for movement. For example, neurons in the brain may die, or the nerves between the brain and the muscle are severed. These disrupt the paths by which electrical signals travel from the brain to neuromuscular groups to effectuate coordinated muscle contraction patterns.

Neuromuscular stimulation devices have been used to deliver stimulation to restore movement to parts of the body not under volitional control. For example, subcutaneous implantable neurostimulation cuffs have been used to block pain and to restore function to damaged or degenerative neural pathways. These implantable cuffs are wrapped around a target nerve and generally include one or more electrodes arranged to stimulate the nerve.

Transcutaneous neurostimulation cuffs behave similarly to implantable cuffs, however there are important differences. Because the electrodes are placed on the surface of the skin, rather than below it, stimulation often can better target skeletal muscle tissue or muscle groups, rather than peripheral nerves located deeper under the skin. Muscular stimulation may be preferable to stimulating major peripheral nerves, e.g. ulnar, median, radial nerves, as stimulating these nerves may cause a patient to feel a tingling sensation and it is more difficult to effect the desired movement. By increasing the number and layout of electrodes in a neuromuscular cuff, similar to the direction taken with implanted nerve cuff designs, current generation neuromuscular stimulation cuffs have been able to selectively stimulate individual muscles or muscle groups and achieve finer movements such as individual finger flexing and extension.

Flexible-like transcutaneous cuffs have been developed which fit around a human appendage such as a forearm to control the wrist or fingers. These flexible cuffs may include sensors which record muscle activity, or electromyography (EMG) signals, and stimulate in response to the EMG signals.

Neurostimulation devices do not, by themselves, resolve the problem of motor impairment due to neural damage, because such a device by itself does not respond to volitional control. For example, the user of a neurostimulation device cannot cause the device to stimulate muscle activity by willing such muscle activity to occur. An effective system for translating human brain signals into desired movements in real time and sending a signal to cause the desired movements has not yet been developed. It would be desirable to provide such systems and methods such that a neural signal indicative of an intended action could effectuate the intended action, either in a damaged neuromuscular region or in an electronic device.

BRIEF SUMMARY

The present disclosure relates to systems and methods for recognizing desired movements from the neural signals of a user in real time, and translating those desired movements into electrical signals to be sent to a target, which can be the user's limb, a prosthetic, or some other electronic device. Thus, it is possible for a chronically paralyzed user to regain movement through the decoding of intracortical signals captured by a brain implant and subsequent routing of those messages to the muscles to accomplish the desired movement.

Various embodiments of continuous methods of creating a neural bridge are disclosed within, which include: measuring a first neural activity of a patient; based on the first measurement of neural activity, determining a desired movement of a target; delivering an electrical signal to the target to start movement of the target and measuring a second neural activity of the patient; and based on the second neural activity of the patient or motion of the target, maintaining or changing the signal being delivered to the target as the target moves, so that the desired movement is achieved.

The methods may further include removing at least one artifact from the measurement of neural activity prior to determining the desired movement of the target. Determining the desired movement may comprise extracting at least one feature from the measured neural activity. The extracted feature may be a signal amplitude, amplitude of the signal in a given frequency range, amplitude of the signal in a wavelet scale, or a firing rate. The determining may further include feeding the at least one extracted feature to a decoder to identify additional features in a higher dimensional space. The decoder may look for patterns in the features that indicate the desired movement. The determining of the desired movement may further include sending the features to both a discrete multiclass decoder and a movement effort decoder, wherein the discrete multiclass decoder determines the desired movement and the movement effort decoder determines a level of movement effort by the patient; and using outputs from the discrete multiclass decoder and the movement effort decoder as inputs for forming the signal delivered to the target.

The outputs from the discrete multiclass decoder and the movement effort decoder can be nonlinearly modified to determine the signal delivered to the target. The subsequent neural activity or the motion of the target can be used to determine a body state of the target, and the signal may be dynamically changed based on the determined body state. Sensor input may be used to determine the body state of the target. A history of feedback provided to the patient may also be used to determine the body state of the target. A patient activation profile may also be used to determine the signal sent to the target. The signal delivered to the target may be a multiplexed signal that includes multiple interleaved signals that do not interfere with each other. The target may be a body limb or a prosthetic limb, a wheelchair, a cursor on a computer, an exoskeleton, a remote control device, or an external robotic arm.

Also disclosed are methods of creating a neural bridge, including: measuring neural activity of a patient; decoding a desired movement of a target based on the measurement of neural activity; and delivering a multiplexed signal to the target, the multiplexed signal containing multiple interleaved signals that do not interfere with each other and produce the desired movement of the target.

Still other additional methods disclosed herein for creating a neural bridge include: measuring neural activity of a patient; determining a desired movement of a target based on the measurement of neural activity; identifying actions about multiple joints of the target that will result in the desired compound movement, and identifying actuating signals to the multiple joints that do not interfere with each other and that will result in the desired compound movement; and delivering a multiplexed signal to the target, the multiplexed signal containing the multiple actuating signals interleaved together, to produce the desired compound movement of the target.

The methods used herein can be used to decode desired movements in real time and use real-time feedback to improve the motion of the target. Compound movements (e.g. simultaneous movement of multiple joints) can also be attained from a single stimulation pattern. Neural signals can be directly processed and then sent to the target to "bridge" any gaps in the normal nerve signal transmission pathways between the brain and the limb whose movement is desired. The systems and methods disclosed herein are particularly advantageous in the treatment of spinal cord injury, stroke, multiple sclerosis, motor neuron disease, and traumatic brain injury. Other advantages will become apparent to one of ordinary skill in the art upon reading and understanding this disclosure.

BRIEF DESCRIPTION OF THE DRAWINGS

The following is a brief description of the drawings, which are presented for the purposes of illustrating the exemplary embodiments disclosed herein and not for the purposes of limiting the same.

FIGS. 7A-18B are pictures of several different hand and arm motions obtained from an experiment in which an able-bodied user was asked to move his hand/arm into a given position. In each set, one picture shows an image of the hand/arm motion that the user performed with his limb, and the other picture shows a graphical hand representation of the user's limb position based on position sensor data collected from the sleeve. In each set of pictures, the actual limb moved is shown as the left hand, and the graphical limb moved was the right hand.

FIG. 7A shows the limb moved for hand pronation, palm down.

FIG. 11A shows the limb moved for supination, palm up, and FIG. 11B shows the measured position in a graphical limb.

FIG. 12A shows the limb moved for wrist extension, and FIG. 12B shows the measured position in a graphical limb.

FIG. 13A shows the limb moved for wrist flexion, and FIG. 13B shows the measured position in a graphical limb.

FIG. 14A shows the limb moved for radial deviation, and FIG. 14B shows the measured position in a graphical limb.

FIG. 18B shows the measured position in a graphical limb.

FIG. 19A shows the percentages for finger extension. FIG. 19B shows the percentages for finger fair curvature. FIG. 19C shows the percentages when a fist is made.

FIG. 22A is for thumb flexion. FIG. 22B is for thumb extension. FIG. 22C is for thumb wiggle.

FIGS. 22A-22C are sets of graphs showing differences in neural activity between electrode channels for three movements: CPG thumb wiggle, thumb extension, and thumb flexion.

FIG. 24A is for CPG thumb wiggle. FIG. 24B is for thumb flexion. FIG. 24C is for thumb extension.

DETAILED DESCRIPTION

Figure 1:
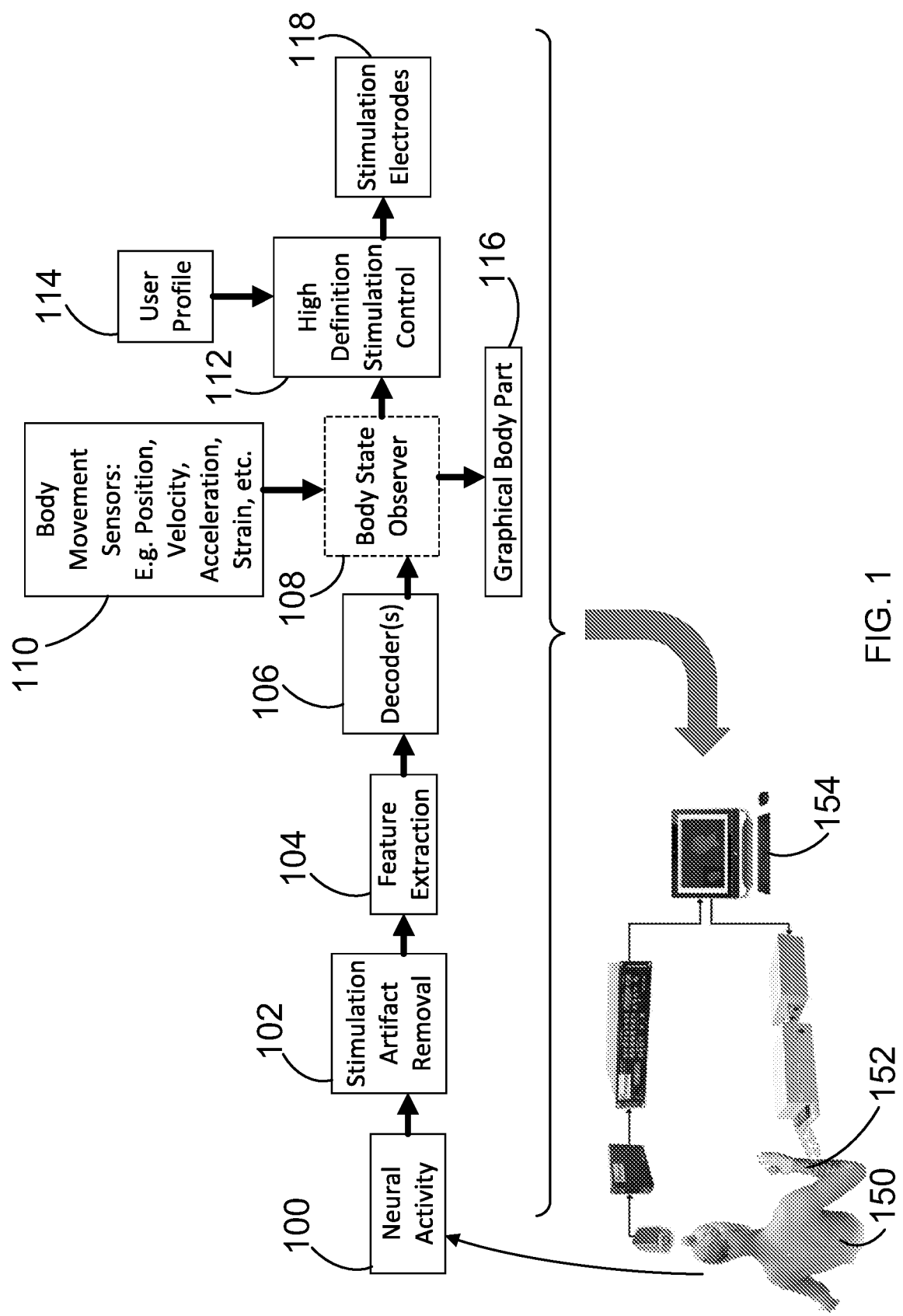
FIG. 1 is a diagram illustrating the methods of the present disclosure for decoding a neural signal to determine the desired movements, and an artificial neuromuscular stimulation system with volitional control for implementing those desired movements.

A more complete understanding of the methods and apparatuses disclosed herein can be obtained by reference to the accompanying drawings. These figures are merely schematic representations and are not intended to indicate relative size and dimensions of the assemblies or components thereof.

Although specific terms are used in the following description for the sake of clarity, these terms are intended to refer only to the particular structure of the embodiments selected for illustration in the drawings, and are not intended to limit the scope of the disclosure. In the drawings and the following description below, it is to be understood that like numeric designations refer to components of like function.

The present disclosure relates to methods for providing an artificial neuromuscular stimulation system with volitional control, e.g. by decoding neural activity to determine a desired movement, then transmit the desired movement to a target to perform the desired movement. For example, these methods would be useful for patients who may have suffered nerve injury to bypass that disruption and "bridge" that gap to send electrical signals to a body limb, for example an arm or leg. Desirably, it would be as if the disruption did not exist; the patient would simply think of the desired movement of the body limb, and that movement would occur. In other embodiments, rather than being a body limb, electrical signals may be delivered to a target that is non-human (e.g. an electronic device). This allows for control of the non-human target by use of the electrical signals. Examples of non-human targets that may be controlled in this way include: a prosthetic limb, a wheelchair, a cursor on a computer, an exoskeleton, a remote control device, and an external robotic arm.

Referring first to FIG. 1, an artificial neurostimulation system provides artificial neurostimulation to a human user 150 under volitional control of the subject 150. The artificial neurostimulation system includes a transcutaneous neurostimulation sleeve 152 for providing electrical stimulation to a body part of the subject 150, and a computer or other electronic data processing device 154 connected to receive neural signals from neural sensors, and to output control signals to the neurostimulation sleeve, and further programmed to determine a volitional intent of the subject based on the received neural signals and to generate the output control signals to implement that volitional intent. The user 150 is assumed to have motor impairment due to neural damage, such that volitional control, that is, simply thinking or intending of a desired motion (e.g. intending to fold two fingers against the palm) does not result in the desired motion. This can occur due to nerve injury between the brain and the fingers. Instead, a computer 154 receives the user's neural activity as an input, and determines the desired motion. The computer then generates an electrical stimulation pattern which is delivered to a neurostimulation sleeve 152, which is worn by the patient on the arm and which includes electrodes. The electrical stimulation of the sleeve 152 results in the desired bending of fingers. The system provides an artificial neural bypass, or neural "bridge", around the injury to provide control of the fingers.

FIG. 1 also illustrates a flowchart/algorithm for determining the desired motion from a user's neural activity and translating that into an electrical stimulation pattern that can be transmitted. First, the neural activity of the user 150 is measured in operation 100 to obtain a neural signal. Noise artifacts are then removed from the neural signal in operation 102. To determine a desired movement, one or more features are extracted from the measured neural signal in operation 104. Subsequently, the extracted feature(s) are sent to decoders in operation 106. The decoders determine the desired movement. That output is then sent to a body state observer 108, which is a model of the various parts of the user's body and the target. Inputs from body movement sensors 110 may also be taken into account in the body state observer 108, which is used to predict future movements that need to be made to obtain the desired movement. In operation 112, high definition stimulation control is used to calculate the stimulation pattern that is needed to obtain the desired movement. A user activation profile 114 containing information on the user's reaction to various stimulation patterns can be used here to customize the resulting stimulation pattern/signal that is determined. That stimulation pattern is then sent to stimulation electrodes 118, which stimulate the appropriate part of the target (e.g. muscle groups, motors, etc.). Alternatively, during training, the system calculates the effect such stimulation would have, and displays this in the form of a graphical body part 116, to provide feedback to the user. This algorithm repeats at a high rate, permitting continuous real-time updating of the stimulation signal to the target. Thus, it should be understood that the methods described herein may be performed either continuously or intermittently.

The measurement of neural activity 100 can be done by any suitable technique. For example, electroencephalography (EEG), a noninvasive technique, may be used. In EEG, electrodes are placed on a scalp of user 150 to measure electrical activity along the scalp. Invasive techniques (electrodes placed beneath the scalp) are also contemplated for use. For example, a "Utah array" of electrodes, such as that made by Blackrock Microsystems, may be used. The Utah array can have up to 96 electrodes. Also contemplated is the use of a "Michigan array" of electrodes, such as that made by NeuroNexus. Such microelectrode arrays would be implanted into the brain, for example in the primary motor cortex. Electrocorticography (ECoG) may also be used. In ECoG, electrodes are placed directly on the exposed surface of the brain to record electrical activity. The location in which the electrodes are implanted can depend on the location of the injury. An appropriate location for implantation can be determined by showing a video of able-bodied movement of the relevant body part to the patient/user while performing functional magnetic resonance imaging (fMRI).

These electrode arrays record "brain waves," more particularly neural signals which are representative of a varied set of mental activities. Neural signals include electrical signals produced by neural activity in the nervous system including action potentials, multi-unit activity, local field potential, ECoG, and EEG. The neural signals from each electrode can be sampled at rates of at least 10 kHz or 30 kHz, providing a robust stream of data (though not all of this data needs to be used). These neural signals are sent wirelessly or, alternatively, through a wired connection, to a neural signal processing device for processing of the neural signals.

Next, the neural signal is processed 102 to obtain a "clean" signal. In this regard, for most purposes, it is desirable for each electrode to record the signal from a given neuron, rather than a set of given neurons. The brain is very busy electrically, and the presence of other neurons in the vicinity of these delicate and sensitive electrodes can create noise that obscures the desired signal. The signals actually detected by the electrode array are first amplified and then filtered to remove noise outside of a frequency band of interest (e.g. 0.3 Hz to 7.5 kHz). The signal may be processed in analog or digital form. Examples of useful analog filters include an 0.3 Hz 1st order high pass filter and a 7.5 kHz 3rd order low pass filter. An example of a digital filter is a digital 2.5 kHz 4th order Butterworth low pass filter. Processing may occur at desirable rates, for example every 100 milliseconds.

Figure 2:
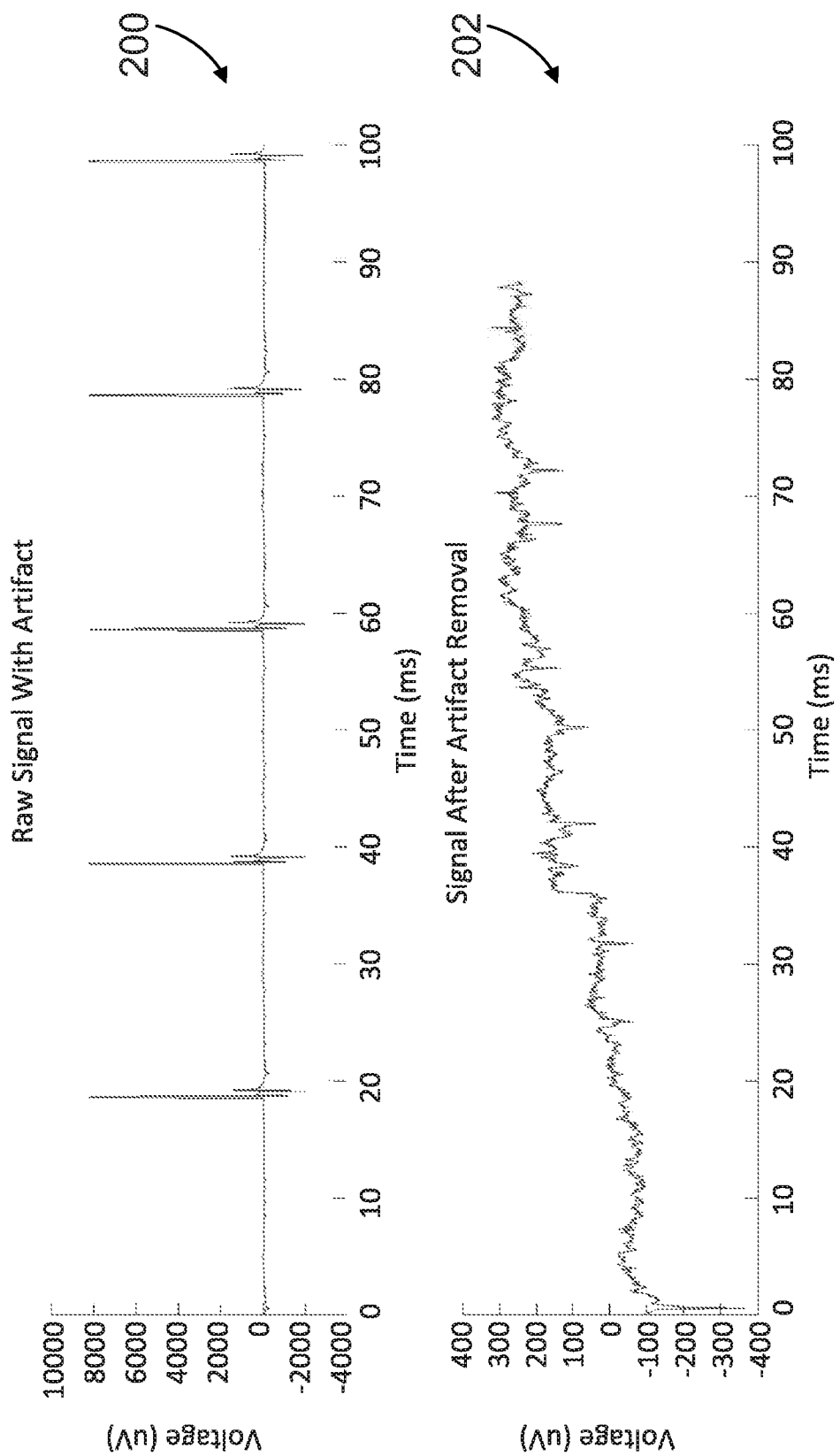
FIG. 2 illustrates plots of a neural signal as a function of time before and after artifact removal. In the "before" graph at top, the y-axis is voltage in microvolts, with the scale ranging from −4000 to +10,000 µV at intervals of 2000 µV. The x-axis is time, with the scale ranging from 0 milliseconds (msec) to 100 milliseconds at intervals of 10 msec. In the "after" graph at bottom, the y-axis is voltage in microvolts, with the scale ranging from −400 to +400 µV at intervals of 100 µV. The x-axis is time, with the scale ranging from 0 milliseconds (msec) to 100 milliseconds at intervals of 10 msec. It can be seen that the "before" neural signal versus time dataset has been processed such that the "after" neural signal versus time dataset is of a shorter duration (about 10% shorter), which is due to removal of signal artifacts.

Part of the processing 102 involves artifact removal. Artifact removal is used to "clean up" the neural activity data and results in improved processing. Artifacts in the data may have been caused by, for example, electrical stimulation in the body limb (e.g. forearm) whose movement is desired. FIG. 2 shows a signal before artifact removal 200, and shows the "same" signal after artifact removal 202. Identification of an artifact may be accomplished by, for example, by detecting a threshold crossing that occurs at the same time on a large fraction of the channels in the signal data. Here, for example, the artifacts are the extremely high peaks up to 8000 µV at periodic rates of ~20 msec. The threshold can be fixed or dynamically calculated, and for example can be modified based on factors already known to the processor such as when electrical stimulation is delivered through the neurostimulation sleeve. A set time window of data may then be removed around the detected artifact. The data is then realigned (e.g. voltage-wise) and then stitched back together (e.g. time-wise). For example, as shown here, the time window is 2.5 milliseconds, based on the system's recovery period for an amplifier. The five peaks are thus removed, and the remaining signal is shown on the bottom. As seen here, once the artifacts are removed, the signal is of much smaller magnitude but contains useful information.

Of course, when data is being measured on multiple channels (e.g. from a 96-channel microelectrode array), the artifact should be removed on each channel. One common method of artifact removal is to determine the average from all or most of the channels, and then subtract the average from each channel. Alternatively, the stimulation signal can be shaped in such a way that artifacts on certain frequencies may be prevented or reduced. In other embodiments, the artifacts can be planned somewhat. For example, the electrical stimulation delivered through the neurostimulation sleeve 152 could have a known shape, such as a square pulse. These will aid in removing artifacts from the neural signal.

Next, in operation 104 of FIG. 1, features are extracted from the neural signal. "Feature" is the term given to various pieces of data, either from each electrode individually or some/all electrodes considered as a group, that can contain useful information for determining the desired movement. Examples of such features include: signal amplitude, amplitude of the signal in a given frequency range, amplitude of the signal in a wavelet scale, or a firing rate. Here, a firing rate may refer to the number of action potentials per unit of time for a single neuron. Again, the extracted features provide useful information about the neural network being monitored. Desirably, the feature has a high signal-to noise ratio, preferably 2 or greater, and more preferably 3 or greater.

One particular set of features is obtained by applying a wavelet decomposition to the neural signals, using the 'db4' wavelet and 11 wavelet scales, as described in Mallat, S. G., *A Wavelet Tour of Signal Processing*, Academic Press (1998), (ISBN 9780080922027). Scales 3 to 6 are used to approximate the power in the multi-unit frequency band spanning approximately 117 Hz to 1875 Hz. The mean of wavelet coefficients for each scale of each channel (of the 96-electrode array) is taken across 100 milliseconds of data. A 15-second sliding window (e.g. boxcar filter) is used to calculate the running mean of each wavelet scale for each channel. The 15-second mean is then subtracted off of the mean wavelet coefficients of the current 100 ms window. The mean subtraction is used in order to account for drift in the neural signal over time. The coefficients of scales 3 to 6 are standardized per channel, per scale, by subtracting out the mean and dividing by the standard deviation of those scales and channels during training. The mean of the standardized coefficients is then taken for each channel. The resulting values are then used as features, called mean wavelet power (MWP), to be inputted to the decoder(s) running in real-time.

In some applications, a Fast Fourier Transform (FFT) may be used to extract features. Advantageously, an FFT may be used for obtaining power information. Additionally, a non-linear or linear transform may be use to map the features to N-dimensional space (e.g. by use of a radial basis function). This may be useful when a desired movement can manifest itself in the form of multiple different electrical signals from the electrodes, so that the system can recognize any of those different signals.

Next, the extracted features are sent to one or more decoders 106 that associate the features with a desired action, movement, thought, or so forth. It is contemplated that decoders can be implemented in at least two different ways. First, as illustrated in FIG. 3A, the extracted features may be sent as input to individual decoders 300. Each decoder has previously been "trained" to associate certain features with a particular movement. Examples of such decoded motions include: individual finger flex or extension; wrist flex or extension; radial deviation; forearm supination or pronation; and hand open or close. Each decoder then outputs a value indicating a strength or confidence that its particular movement has been identified. For example, each decoder may use a nonlinear kernel method (e.g. Gaussian radial basis) with a non-smooth support vector machine (SVM) that uses sparsity optimization to zero out features that are least relevant to the motion being identified by that particular decoder. Advantageously, use of the decoders allows for a determination of related, simultaneous movements. For example, the decoders may determine that a hand is closing with either the arm moving or not moving. In addition, each decoder may determine a level of effort associated with its motion. Also, the dataset used by the decoder to determine its output may be based on only a certain amount of history, so that the decoder adapts to changes in the neural signal over time.

Figure 3B:
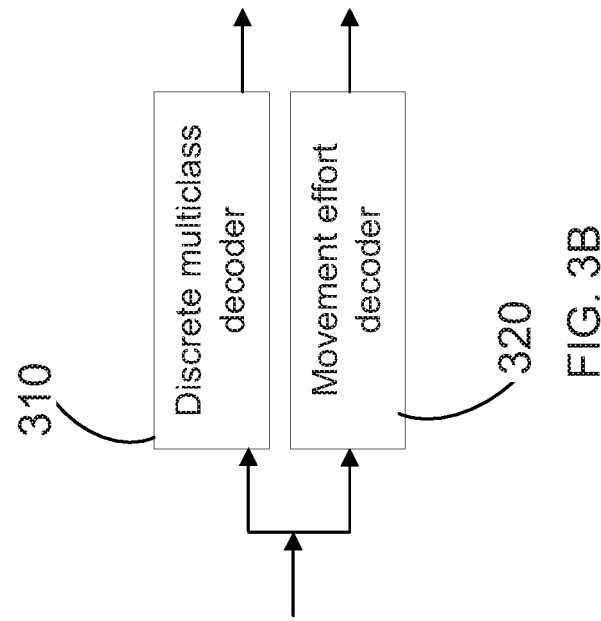
FIG. 3B shows a discrete multiclass decoder and a movement effort decoder, which is another suitable illustrative embodiment of the decoder(s) of the system of FIG. 1. The multiclass decoder can be considered an amalgamation of the single-motion decoders illustrated in FIG. 3A. The movement effort decoder outputs a measure of the focus level being applied to attain the desired movement.
Figure 3A:
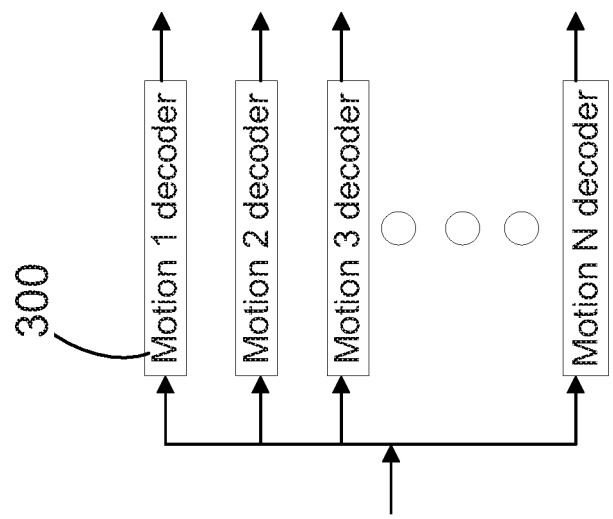
FIG. 3A is a diagram indicating single-motion decoders, which provide simple binary output (yes/no) to identify a desired movement and are suitable illustrative embodiments of the decoder(s) of the system of FIG. 1.

Alternatively, as illustrated in FIG. 3B, the decoders can be organized in the form of a discrete multiclass decoder 310 that is used in parallel with a movement effort decoder 320. The discrete multiclass decoder determines the motion(s) that is being imagined. For purposes of this disclosure, the multiclass decoder can be considered as a software module that receives the features as input, and can output any one of multiple desired movements. The movement effort decoder determines the level of movement effort of the identified desire movement(s). Any decoded signal may be linearly or nonlinearly mapped to determine a signal delivered to the target. In general, the system can determine both the user's movement intention before the physical movement begins, and also during movement as well. Again, it should be noted that the neural signals from the user are for movements that may be imagined or attempted, as well as actually performed.

Next, the output of the decoders is sent to a "body state observer" 108. The body state observer is a physics-based dynamic model of the body (e.g. including body parts such as arm, hand, leg, foot, etc.) implemented as software. The body state observer takes the desired forces, torques or so forth as inputs and continuously updates and outputs the velocity and position estimates of the actual body part(s). The body state observer can also accept data from body movement sensors 110 as input. Such sensors may provide information on the position, velocity, acceleration, contraction, etc. of a body part. For example, sensors could provide information on the position of the elbow relative to the shoulder and the wrist, and how these body parts are moving relative to each other. In addition, the body state observer has a "memory" or a history of the feedback previously provided to the user.

The use of a body state observer is considered to have at least two advantages. First, the outputs of the body state observer can be used to continuously or dynamically change the stimulation patterns being outputted to the neurostimulation sleeve, to account for changed circumstances. For example, if the stimulation electrodes are transcutaneous, they can move with respect to their target muscles as the joints move (e.g. pronation/supination). The stimulation pattern given through the stimulation electrodes can thus be modified according to the relative shift between electrodes and muscles. In other words, the stimulation pattern may be dynamically changed (or held constant) based on a determined body state. This dynamic change in the stimulation pattern may be referred to as electrode movement compensation (EMC). In one example of EMC, a stimulation pattern may be changed based on whether a user's palm is up or down. Second, for transcutaneous electrodes and even implanted electrodes, the force or torque at a given stimulation current is often a function of joint position, velocity, or so forth. As the observer predicts joint position and velocity, the stimulation current can be adjusted accordingly to maintain a force or torque desired by a user.

Examples of body states considered by the body state observer include palm up or palm down; arm moving or not moving; a flexing, extension or contraction of a wrist or other body part; and positions or movements of joints.

As another example, the body state observer can use the decoder outputs to estimate angular force at the joints corresponding to the desired motion using a model of the hand and forearm with 18 degrees of freedom. The model estimates the force caused by the contraction of the muscle, the force opposing the muscle contraction due to the anatomy of the hand and forearm, a damping force, and the force of gravity. The output of the model is an estimate of the position of the hand and forearm in real-time, taking into account the history of the stimulation provided to the forearm in order to estimate a current position of the hand and forearm.

Based on the output of the body state observer, the electrical stimulation pattern that is to be sent to the neurostimulation sleeve is determined by an encoding algorithm that generates the appropriate spatiotemporal patterns to evoke appropriate muscle contractions. The present disclosure permits high definition stimulation. In high definition stimulation, the simulation pattern to the electrodes is "continuously" updated. For example, the stimulation pattern to the electrodes is updated once every 0.1 seconds (e.g. 10 Hz). However, shorter and longer update times are also contemplated; in fact, speeds up to 50 Hz are contemplated. As discussed above, the simulation pattern is provided based on the decoded motion(s) and is adjusted based on body states determined by the body state observer. To create a smoother motion, a nonlinear or linear mapping may be applied to the output of the decoder(s). The user's particular user activation profile 114 can also be used to modify or determine the electrical signal that is sent to the target. In this regard, different patients need a different stimulation pattern to obtain the same movement of the target. Advantageously, this allows for delivery of a more effective stimulation pattern based on the individual characteristics of a user. The stimulation pattern is then sent to the electrodes 118 to be transmitted to the muscles.

The stimulation pattern may be driven by the relative magnitude of decoder outputs. For example, the system generally has multiple simultaneously running decoders for individual motions such as wrist flexion, wrist extension; thumb flexion, thumb extension, etc. Each decoder has an output value (e.g. a value between −1 and +1), indicating the likelihood that the particular motion of that decoder is the desired movement, with −1 being unlikely and +1 being very likely. The decoder with the greatest magnitude is taken to be the intended movement. The magnitude of the decoder output can also used to drive the intensity of the stimulation, or the full stimulation intensity for the desired motion can be used.

Additionally, in high definition stimulation, multiple signal patterns may be interleaved (e.g. by multiplexing) if more than one motion is desired (e.g. a compound motion). For example, the stimulation pattern needed to lift the arm may be directed to different muscles than those for rotating the wrist. Interleaving permits multiple stimulation patterns to be combined into a single stimulation signal sent to the neuromuscular sleeve, so that multiple movements can occur at the same time. Again, this permits the body limb to move more naturally. In addition, advantageously, interleaving prevents electric field patterns created by one stimulation pattern from interfering with electric fields created by another stimulation pattern. This increases the number of complex motions that the system is capable of. However, there is a practical limit to the number of stimulation patterns that may be interleaved due to the fact that when the pulse rate for a single simulation pattern becomes too low (e.g. less than 10 pulses per second), muscle twitches will start to become noticeable and movement smoothness becomes undesirable. Still, interleaving is very effective, and allows for multiple movements to be performed simultaneously (e.g. in a compound movement). This could not be achieved with only a single simulation pattern.

In this regard, the system is able to make the following isolated motions: pinky flexion; pinky extension; ring flexion; middle flexion; middle extension; index flexion; index extension; thumb flexion; thumb extension; thumb abduction; thumb adduction; thumb opposition; wrist flexion; wrist extension; wrist ulnar deviation; wrist radial deviation; forearm pronation; and forearm supination. These motions can be joined together to create combined/compound movements. For example, all of the fingers are flexed at the same time to create a "hand close" motion.

In addition, motions may be sequenced. One example of this in a natural system is a central pattern generator (CPG), which produces rhythmic patterned outputs without sensory feedback. The software/systems of the present disclosure can mimic CPGs by producing a repeatable sequence of events, for example to return a targeted body part to an initial state. Another example of sequenced motions is a functional series of motions. Examples of functional series of motions include: teeth brushing, scratching, stirring a drink, flexing a thumb, cylindrical grasping, pinching, etc. These motions allow for manipulation of real-world objects of various sizes.

As a result of the stimulation 118, the target moves as desired by the user. The electrical stimulation can be provided in the form of current-controlled, monophasic pulses of adjustable pulse rate, pulse width, and pulse amplitude which can be independently adjusted for each channel. For example, the pulse rate may be about 50 Hz, the pulse width may be about 500 microseconds (μsec), and the pulse amplitude can be from 0 to about 20 milliamperes (mA), which can be changed every 100 milliseconds. This cycle repeats continuously until the desired movement is achieved/attained. The stimulation signal/pattern sent to the electrodes can be changed continuously through each cycle if needed, or can be maintained, in order to obtain the desired movement. The software can monitor either or both the neural activity and the motion of the target as detected by the sensors. It is noted that the neural signal may not simply remain constant from the beginning of a desired movement until the end of a desired movement. Rather, for example, as an arm is moving, the neural signal will change. This is because the body is providing dynamic information to the brain on features such as the position and velocity of the moving arm. The software can distinguish between these changes in neural activity based on time. Alternatively, the stimulation signal sent to the target may be actively changed due to changes in the body state, for example due to the shift in the electrode position relative to their targeted muscle groups as a body limb moves. It is also contemplated that the user will be able to control both paralyzed and non-paralyzed muscles simultaneously to achieve complex tasks. Desirably, the decoder is also robust to context changes (such as arm position and speed) that are due to any stimulus that might change the firing pattern/neural activity when the user thinks about a given motion. Some examples of context changes which might arise in the use of the system include: the user using an able-bodied limb while also receiving stimulation to move an impaired limb; the user receiving different types of tactile or visual feedback; or the user having different emotional states (attentive, excited, fatigued, etc)

Figure 4:
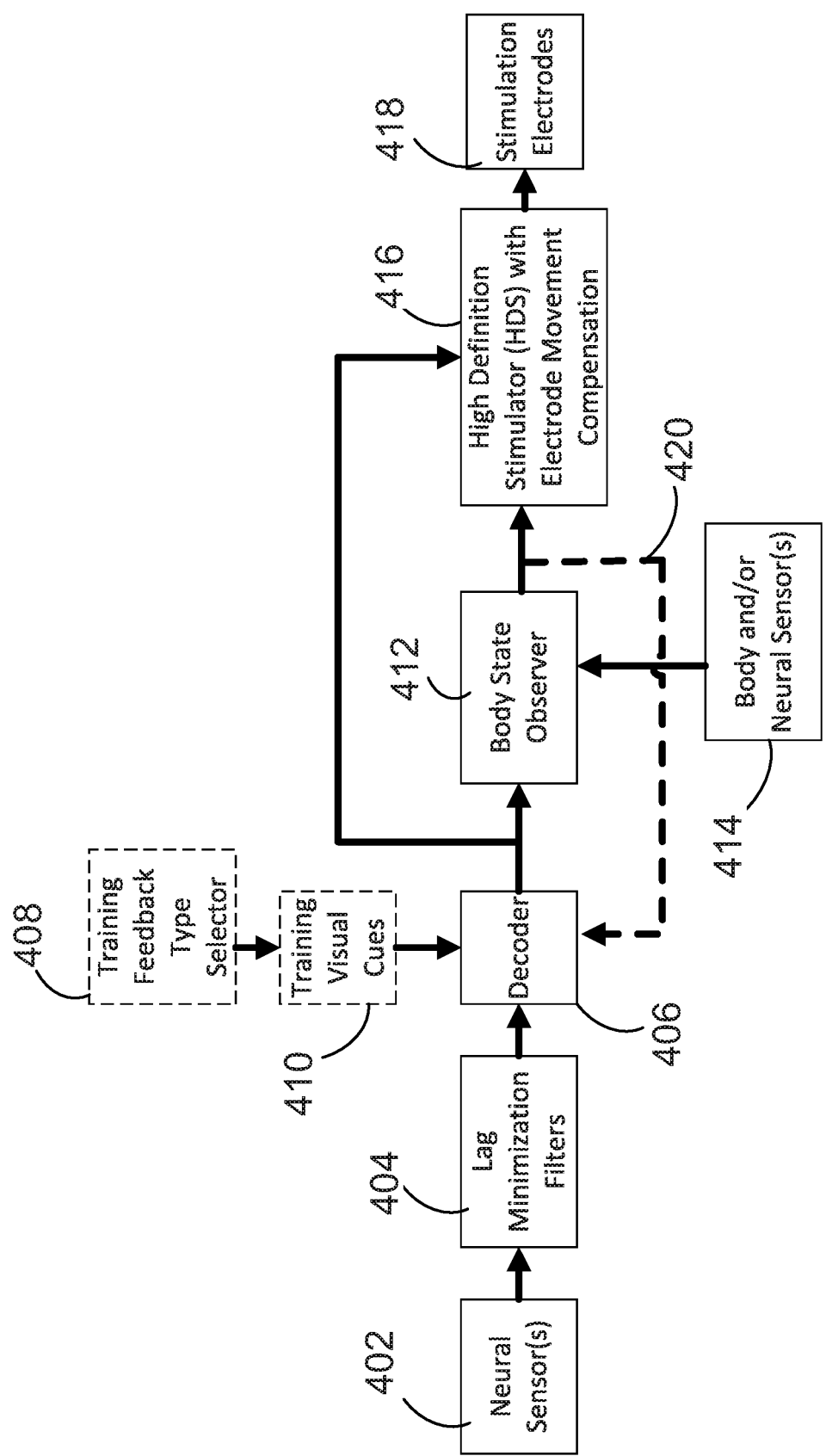
FIG. 4 is a diagram illustrating additional features of the methods described herein, also including boxes showing how the decoders are trained to identify desired movements from a neural signal.

In order to successfully operate, the software must be trained in decoding the neural signal to determine the desired movement. FIG. 4 shows a flowchart related to such training. This flowchart is very similar to that of FIG. 1. Neural sensors 402 record a neural signal which is sent to lag minimization filters 404. The lag minimization filters 404 use a priori statistical information about the neural sensor signals and use the least amount of history to filter the signals (minimizing lag and attenuation that fixed time window filters impose). In addition, during decoder training, a training feedback type selector 408 operates in conjunction with training visual cues 410. The visual cue of operation/component 410 may be provided in the form of a graphical body part 510 (shown in FIG. 5). In this way, the user may attempt or imagine a movement that the user is being shown, for example, by graphical body part 510, and then the user will produce neural signals that are useful in training a decoder 406 to identify the movement being shown. The dots for training feedback type selector 408 and training visual cues 410 indicate that these boxes are used only for training, not during actual operation of the system.

In one related example of decoder training, a user may close his hand with his arm either moving or not moving while the decoders continuously search for patterns. The decoder 406 receives inputs from both the lag minimization filters 404 and the training visual cues 410. In addition, during decoder training, the decoder 406 also receives an input from a body state observer 412, which is shown by dashed line 420. The body state observer itself receives input from body and/or neural sensors 414. The decoder thus receives feedback that helps it to identify the signals indicative of a particular movement. Stimulation is also provided via stimulator 416 to electrodes 418, so that any change in neural activity due to the desired movement is reflected in the input from the neural sensors 402.

Additionally, in decoder training, suitable machine learning techniques may be employed. For example, support vector machine (SVM) techniques may be used. During training, cues (e.g. visual, aural, etc.) may be presented to the user while neural data is collected. This data is collected for various positions over many different contexts in which the user might be thinking about a certain motion, to provide better training data. For each point in time that a feature is calculated, the corresponding cue may be recorded in the cue vector. In some embodiments, neural training data for both static movements and dynamic movements can be combined (or 'blended') and used input to a nonlinear SVM. After training, a decoder may be built using the feature matrix and cue vector. A decoder is typically built by solving for weights matrix 'w' and bias 'ſ' using suitable machine learning techniques to perform classification (e.g. discrete output) or regression (e.g. continuous output). Examples of methods that can be used to build the decoder include: Linear Discriminant Analysis, Least Squares Method, and Decision Trees such as Random Forest Type. The inputs and/or outputs to the decoder can be filtered (e.g. smoothed over the time domain) as well by using low-pass, high-pass, band-pass, Kalman, Weiner, etc. type filters. Multiple decoders may be built (e.g. individual motion decoder, discrete multiclass decoder, movement effort decoder, etc.). Individual movement decoders or a movement effort decoder can be used in real-time to decode the intended force 'F' by using F=A*w−Γ where 'A' is the vector of features for the current point in time.

Additionally and advantageously, decoders are trained to recognize both discrete type motions and rhythmic type motions. A discrete type motion is generally a single movement. In contrast, rhythmic type motions involve multiple, repeatable "sub-motions." Rhythmic type movements are used in daily activities such as teeth-brushing, cleaning/scrubbing, stirring liquids, and itching or scratching. Notably, when a user imagines a rhythmic movement, the user's neural activity pattern is different than when the user is imagining a non-rhythmic movement, and identifying these patterns sooner can help the resulting movements be more natural.

In one example, three stimulation levels corresponding to a low, medium, and high evoked force response are provided to a user. A piecewise-linear interpolation is used to construct a mapping for decoder output to stimulation amplitudes for each motion. During real-time decoding, this mapping allows for smooth physical transitions from one movement to the next, controlled by the modulation of intracortical signals. A single point calibration combined with linear interpolation is insufficient due to the non-linear response of the arm to electrical stimulation of varied amplitudes. At lower intracortical modulation levels, the stimulation produced would not be strong enough to evoke the desired motion. The three point calibration facilitates the initiation of the motion in the cases of lower modulation levels.

Figure 5:
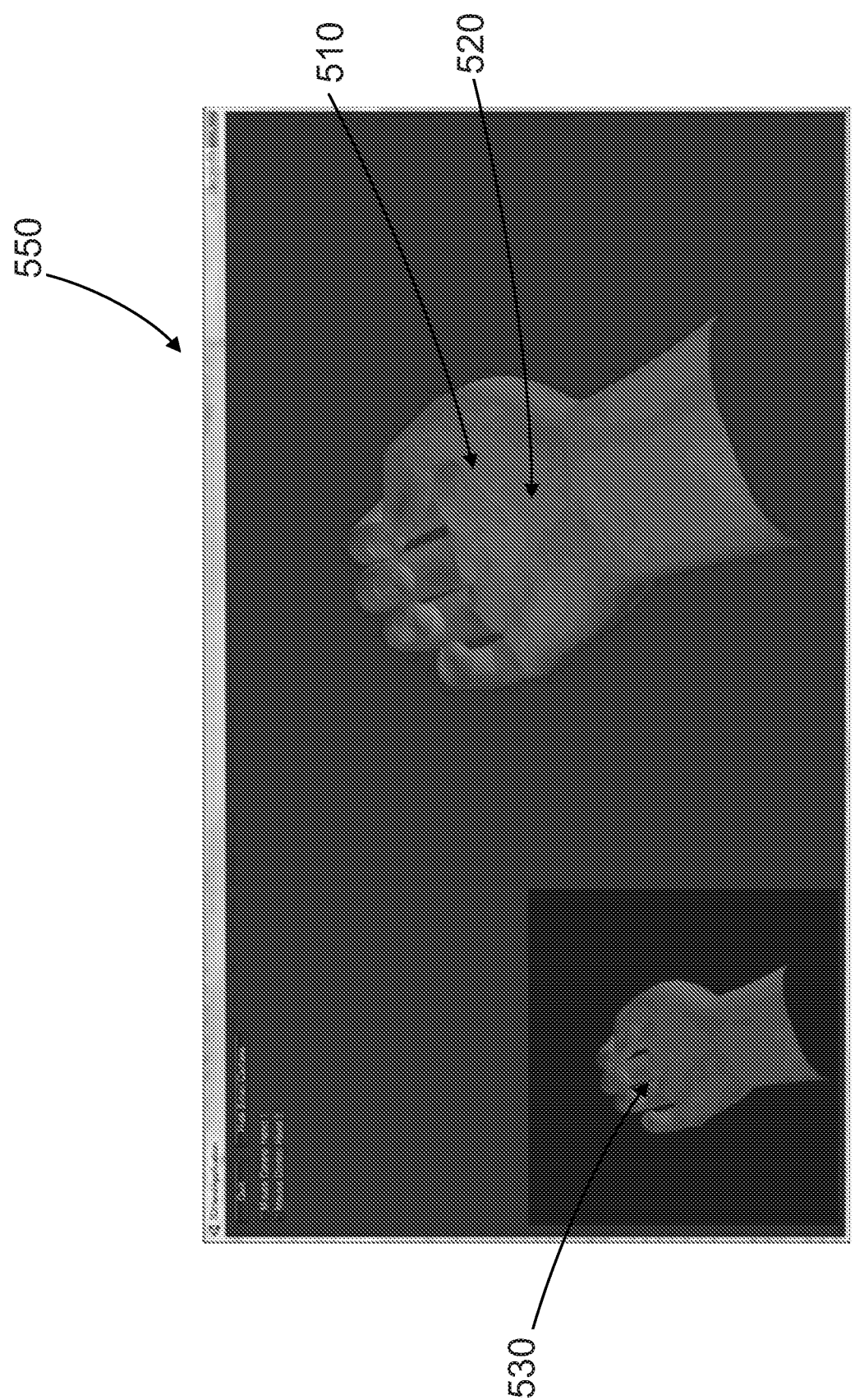
FIG. 5 shows an illustrative graphical user interface display depicting a human hand, which may be shown on the computer display of the system of FIG. 1.

Referring now to FIG. 5, the display of a graphical body part can be advantageously used for decoder training and real-time feedback to the user. Here, a graphical body part 510 is displayed on a graphical user interface (GUI) 550. The graphical body part 510 may be in the form of a large hand 520 and/or a small hand 530. In one example, the small hand 530 is used to show the user the desired movement. The user may then attempt to perform the movement by thinking about it. The large hand 520 provides feedback to the user on how well s/he is doing. For example, the small hand 530 can be controlled by an executable macro that provides cues to the user, while the large hand 520 is controlled by the body state observer 108. In this way, the user is provided with both visual feedback (from the large hand 520) as well as electrical simulation feedback (from the electrodes). The data collected is used to "train" the decoder for the particular movement. This is repeated for multiple different potential movements.

In some embodiments, while the user is attempting or imagining a movement cued by the GUI 550, electrical simulation may be applied to the user in order to help evoke the cued movement. Therefore, the electrical stimulation operates both to provide feedback to the user and evoke the cued movement.

Additionally, a movement depicted on GUI 550 may be a rhythmic type movement (in contrast to a discrete type movement). Rhythmic type movements are used in daily activities such as teeth-brushing, cleaning/scrubbing, stirring liquids, and itching or scratching.

To test the decoders, the user is asked to imagine the movements again, and the system is used to decode their thoughts in real time. While continuously decoding, the system also stimulates the electrodes on the limb to evoke the decoded movement, providing feedback to the user.

The GUI 550 also allows a user to shape the average current during simulation of a given electrode pattern. For example, if it is desired to cause a forearm to be pronated, a user may select a stimulation pattern with average current decays to 0 mA over the course of 1.5 seconds with the decay occurring proportional to $\cos(t^2)$. The stimulation may be updated, for example, at a rate of 10 updates per second. An operator of the GUI 550 may use the GUI 550 to select, for example, simulation signal amplitude or shape, a spatial configuration of the electrodes, simulation patterns in a sequence (e.g. to test a sequence of motions), or so forth. The GUI 550 may also indicate a deflection or force of the user (e.g. firm or weak grip).

Figure 6:
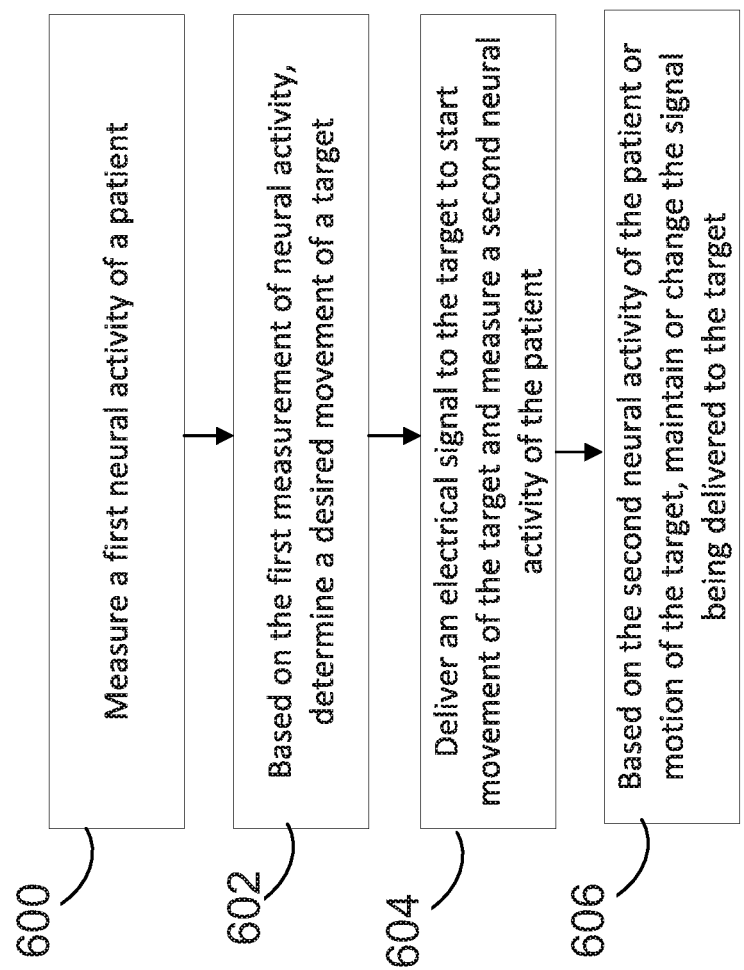
FIG. 6 is a flowchart of an exemplary neuromuscular stimulation method suitably performed in conjunction with the system of FIG. 1, which includes corrective feedback.
Figure 7A:
Figure 7B:
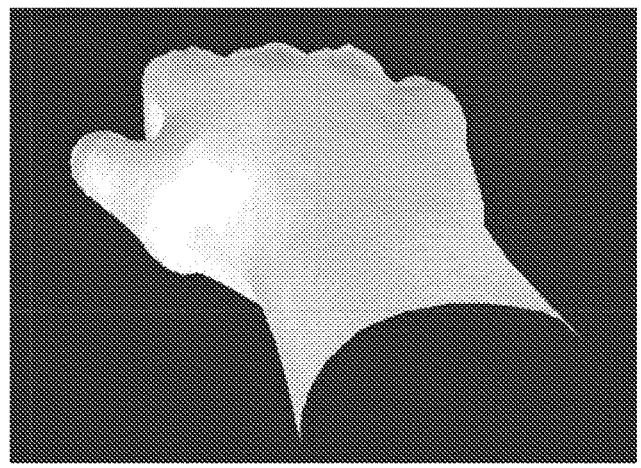
FIG. 7B shows the measured position in a graphical limb.
Figure 8A:
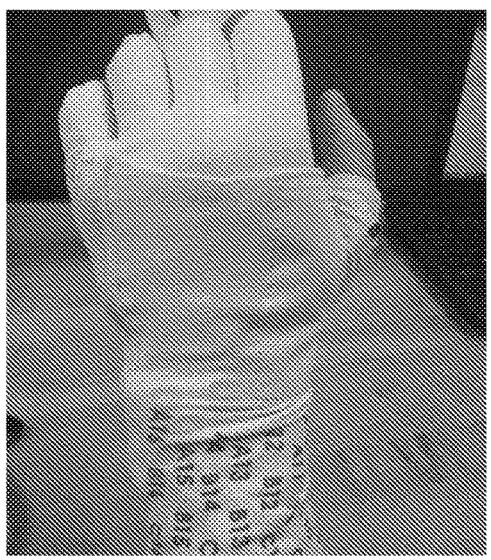
FIG. 8A shows the limb moved for perpendicular arm lift.
Figure 8B:
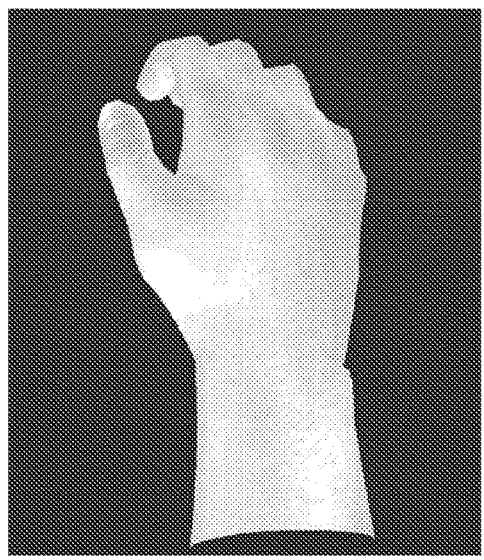
FIG. 8B shows the measured position in a graphical limb.
Figure 9A:
FIG. 9A shows the limb moved for hand neutral position.
Figure 9B:
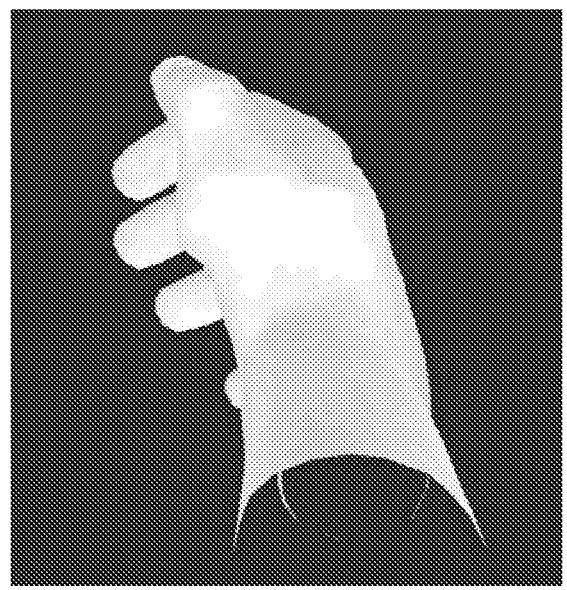
FIG. 9B shows the measured position in a graphical limb.
Figure 10A:
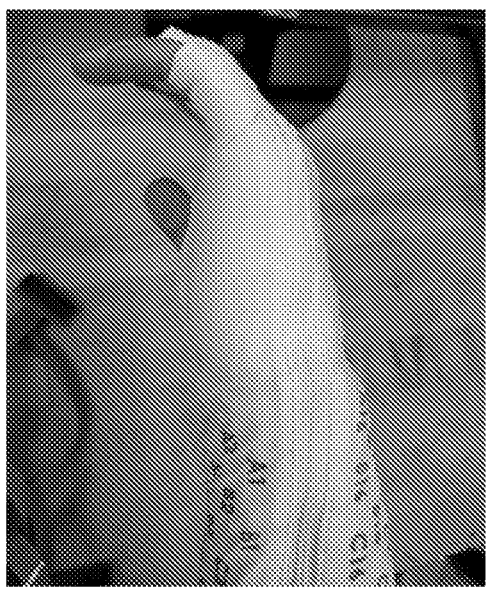
FIG. 10A shows the limb moved for hand pronation, thumb down.
Figure 10B:
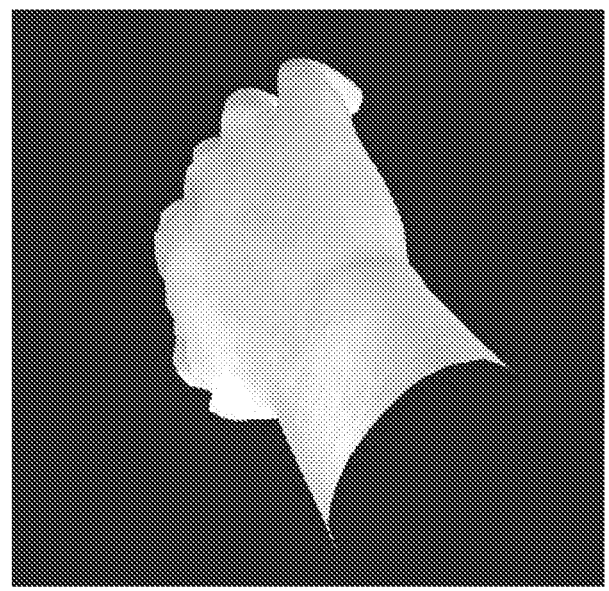
FIG. 10B shows the measured position in a graphical limb.
Figure 15A:
FIG. 15A shows the limb moved for ulnar deviation.
Figure 15B:
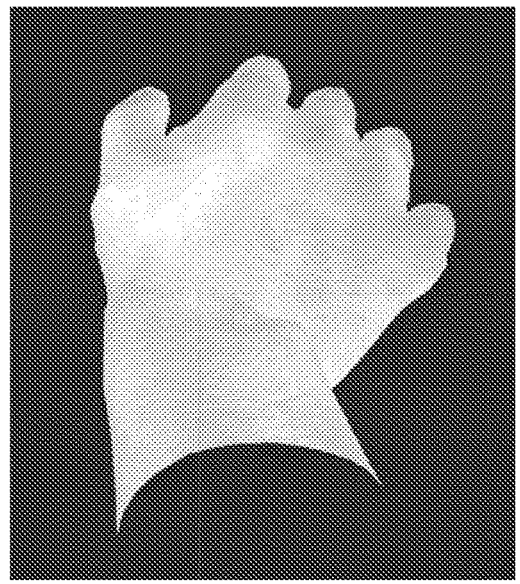
FIG. 15B shows the measured position in a graphical limb.
Figure 16A:
FIG. 16A shows the limb moved for finger extension.
Figure 16B:
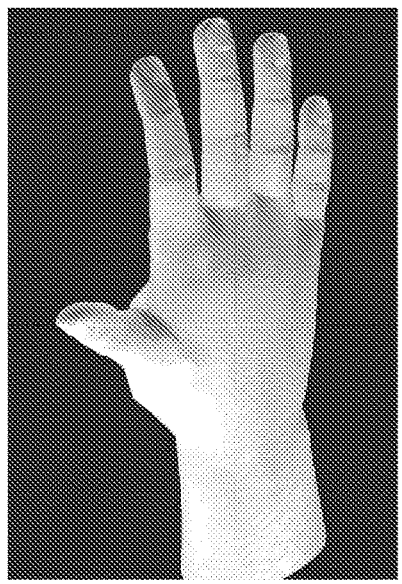
FIG. 16B shows the measured position in a graphical limb.
Figure 17A:
FIG. 17A shows the limb moved for finger fair curvature.
Figure 17B:
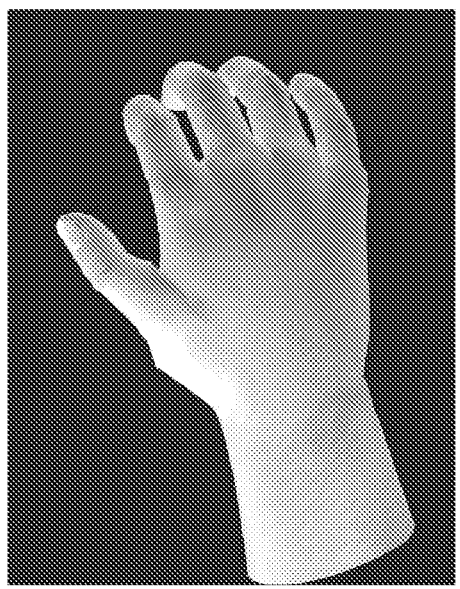
FIG. 17B shows the measured position in a graphical limb.
Figure 18A:
FIG. 18A shows the limb moved for closing the fingers into a fist.
Figure 18B:
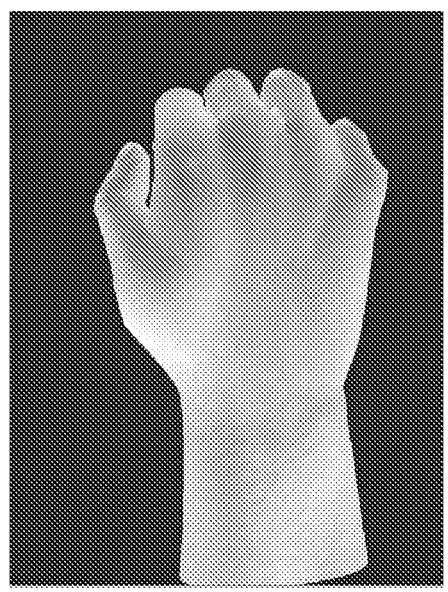

FIG. 6 shows an illustrative example of the methods described herein. In operation 600, a first measurement of neural activity is taken. In operation 602, based on the first measurement of neural activity, a desired movement of a target is determined. In operation 604, an electrical signal is delivered to the target to start movement of the target, and a second neural activity of the user is measured. In operation 606, based on the second neural activity of the user, the signal being delivered to the target is maintained or changed. This cycle repeats itself continuously, so that the desired movement is achieved in real time. Unexpectedly, it was found that during even large changes in neural activity, the electrical signal delivered to the target should sometimes be maintained rather than changed to produce a desired movement.

It will further be appreciated that the disclosed techniques may be embodied as a non-transitory storage medium storing instructions readable and executable by a computer, (microprocessor or microcontroller of an) embedded system, or various combinations thereof. The non-transitory storage medium may, for example, comprise a hard disk drive, RAID or the like of a computer; an electronic, magnetic, optical, or other memory of an embedded system, or so forth.

The processes and systems of the present disclosure are illustrated in the following non-limiting examples.

EXAMPLES

Example 1

FIGS. 7A-18B are pictures taken from a set of experiments where an able-bodied user's left hand was wrapped with a neuromuscular electrical stimulation sleeve. The user was asked to move his hand into different positions. In each set, one picture shows an image of the hand/arm motion that the user performed with his limb, and the other picture shows a graphical hand representation of the user's limb position based on position sensor data collected from the sleeve. In each set of pictures, the actual limb moved is shown on the left hand (the A picture), and the graphical limb moved is shown on the right hand (the B picture). This was due to the setup of the system. As seen here, the correspondence between the measured position shown by the graphical limb and the actual limb movement corresponded very well.

Figure 19A:
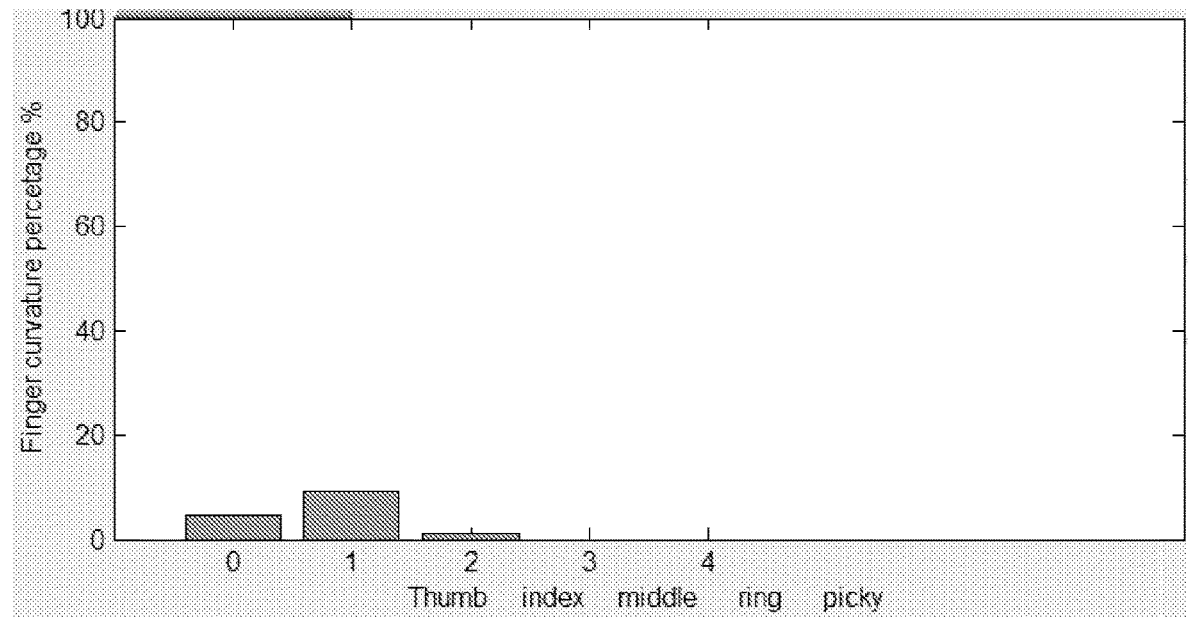
FIGS. 19A-19C are bar graphs showing the different percentages of curvature for each digit during finger extension, finger fair curvature, and making a fist. For each graph, 0 corresponds to the thumb, 1 corresponds to the index finger, 2 corresponds to the middle finger, 3 corresponds to the ring finger, and 4 corresponds to the pinky finger. The y-axis is the finger curvature percentage, and runs from 0% to 100% in intervals of 20%.
Figure 19B:
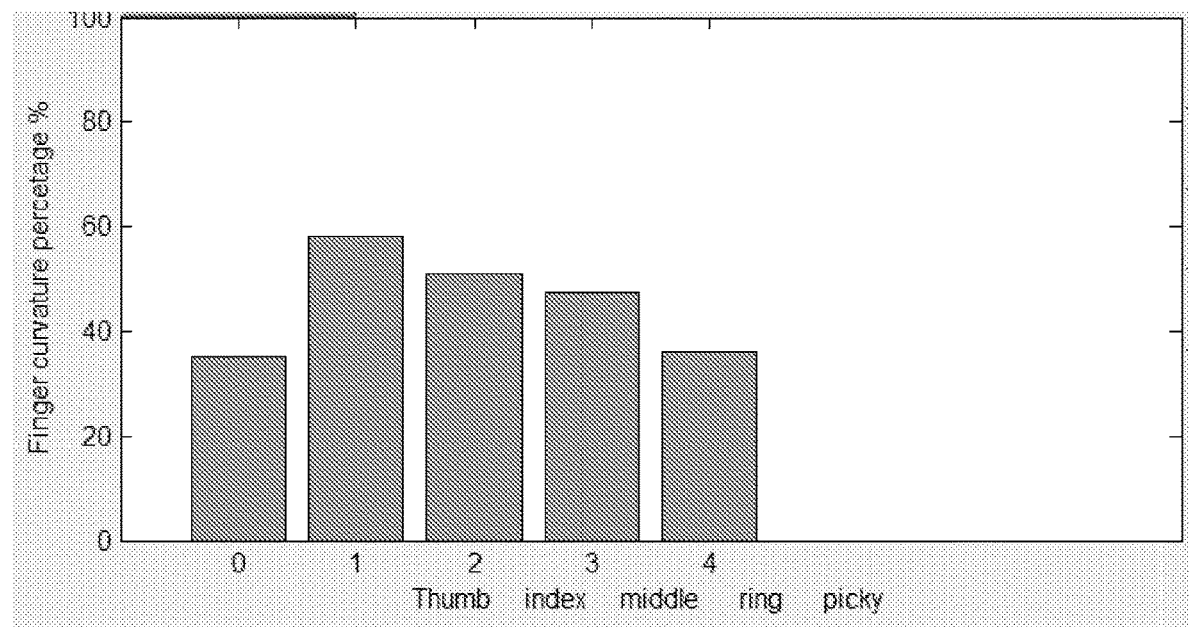
Figure 19C:
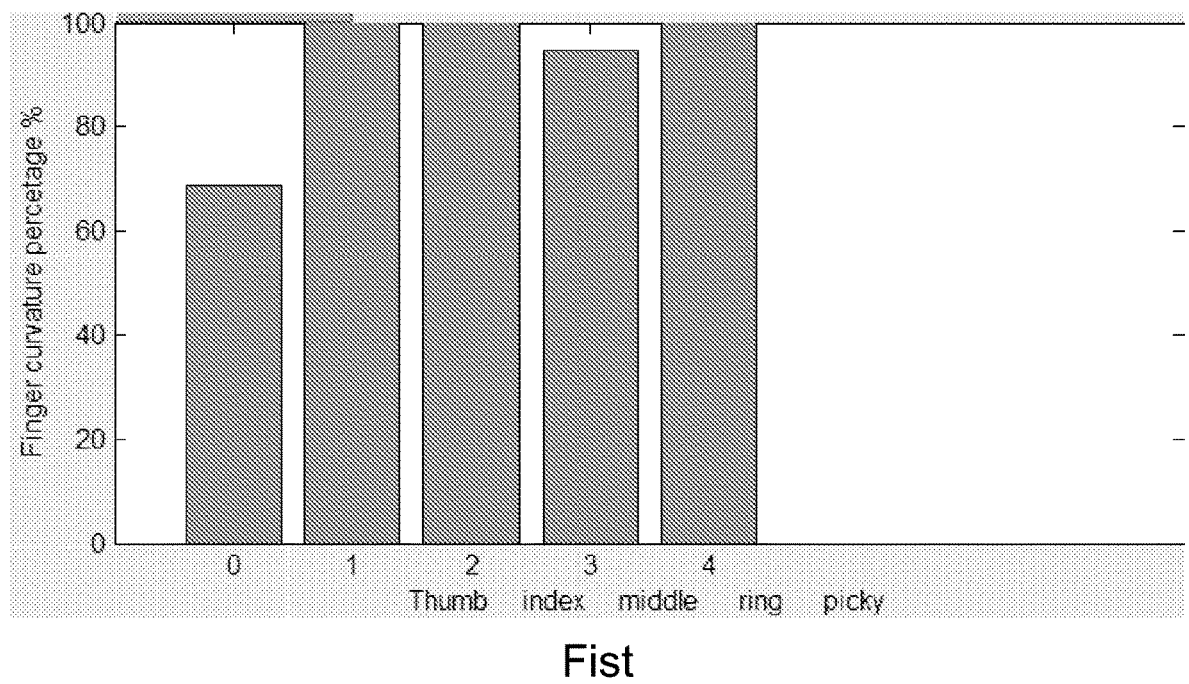

FIGS. 19A-19C are bar graphs showing the different percentages of curvature for each digit during finger extension, finger fair curvature, and making a fist. As seen in FIG. 19A, the digits were generally straight for finger extension, with only three digits having any curvature, and all of them being less than 20% curvature. In FIG. 19B, all of the digits were curved about halfway during finger fair curvature. In FIG. 19C, all of the digits were curved near their maximum, as desired. These illustrate the accuracy of the position sensors and the software that processes their output.

Example 2

Cortical control of rhythmic movements which originate in the brain but are coordinated by Central Pattern Generator (CPG) neural networks in the spinal cord has not been demonstrated previously. Experiments were conducted on a patient with a paralyzed limb to demonstrate that the present system could decode cortical activity and emulate spinal cord CPG function allowing volitional rhythmic hand movement. The technology used a combination of signals recorded from the brain, machine-learning algorithms to decode the signals, a numerical model of CPG network, and a neuromuscular electrical stimulation system to evoke rhythmic movements. Using the neural bypass, a quadriplegic participant was able to initiate, sustain, and switch between rhythmic and discrete finger movements, using his thoughts alone.

Many rhythmic activities, such as breathing, walking/running, stirring, teeth-brushing, scratching, or playing a musical instrument, are initiated in the brain but also require further downstream coordination in the spinal cord. Networks of neurons in the spinal cord known as Central Pattern Generators (CPGs) are responsible for producing these rhythmic activities. CPGs integrate input signal from the brain without sensory feedback from the limbs to produce rhythmic movements.

The results showed that: 1) stable rhythmic oscillations can be generated using a virtual CPG oscillator, 2) neural activity in the motor cortex is distinct for imagining rhythmic movements compared to discrete movements, 3) neural decoders can be trained to successfully classify imagined rhythmic versus discrete movements, and 4) the decoded neural activity in combination with the CPG oscillator and NMES can differentially enable rhythmic versus discrete movements in a paralyzed finger.

Setup

Figure 20:
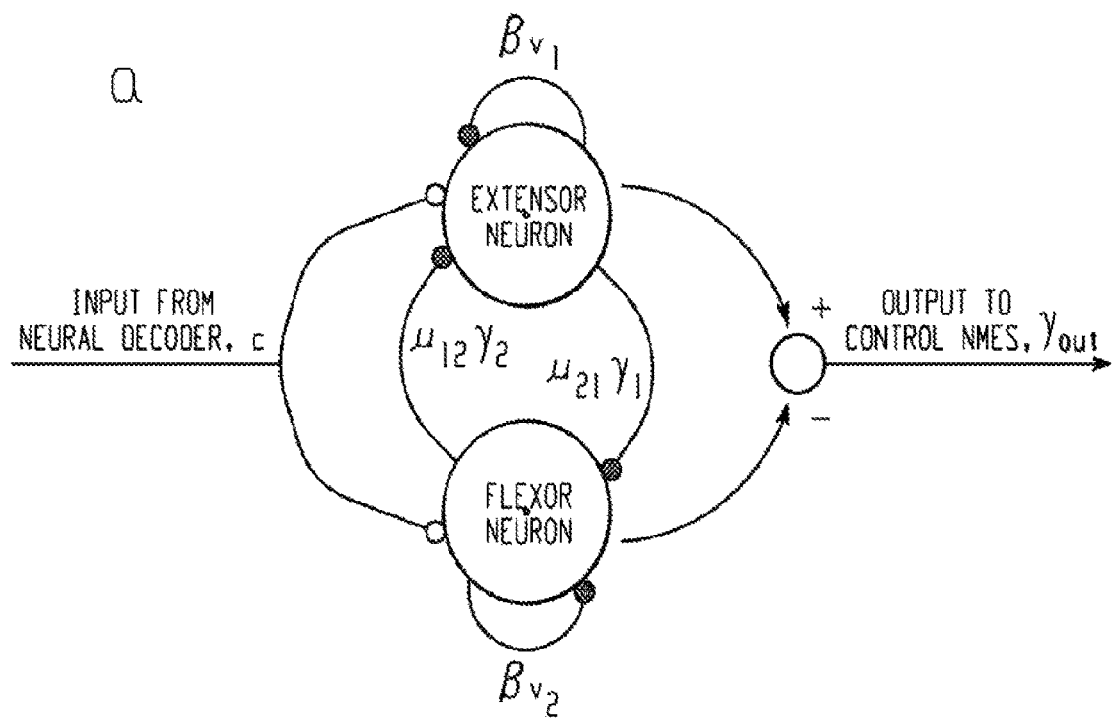
FIG. 20 is an illustration of a two-neuron oscillator based on the Matsuoka neural model, which was used to simulate a central pattern generator (CPG).

Initially, the CPG oscillator model used to generate oscillatory/rhythmic patterns was based on the biologically inspired two-neuron oscillator as described by Matsuoka (*Biol. Cybern.*, 1985, 52(6): pp. 367-76) in which two neurons (the extensor neuron and the flexor neuron) are interconnected in a mutually inhibitive network as illustrated in FIG. 20.

The CPG oscillator is capable of generating oscillatory output, the amplitude and frequency of which can be independently controlled by tuning the parameters. The amplitude is positively correlated to the tonic input c. The frequency is positively correlated to the adaptation coefficient $\beta$ and negatively correlated to the time constants $\tau 1$ and $\tau 2$. The v represents the membrane current, $\mu$ the weight of the interaction between the neurons, y is the neuronal output. Parameters were selected to generate stable oscillations at 2.5 Hz. This frequency was selected due to hardware and software limitations as the rate at which the neuromuscular stimulator could be updated was limited to 10 updates/sec, and the muscles required approximately 0.2 sec of continuous stimulation of the stimulation pattern in order to achieve measureable deflection of the thumb. Similarly the output amplitude of the CPG oscillator was discretized, which was used to trigger the maximum flexion/extension stimulation of the thumb in order to achieve the maximum deflection that was physically possible for the thumb.

Figure 21:
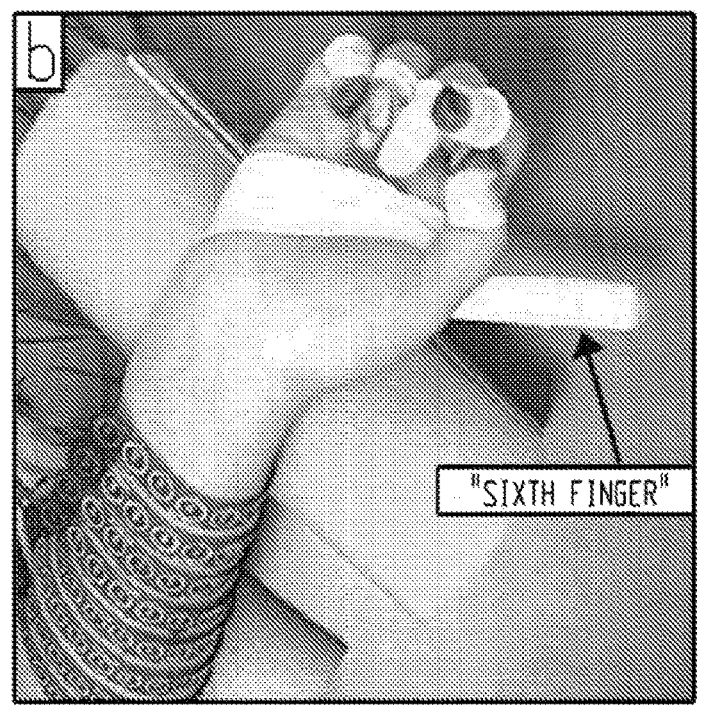
FIG. 21 is a picture of a hand with a "sixth" finger that served as a reference point for measurement during testing.

FIG. 21 shows the test setup for measuring hand motion. To quantify thumb movements and measure performance, colored finger cots were placed on the participant's hand during testing. For added sensitivity in detecting movements involving the wrist (used as reference), an additional cot was placed on a plastic cylinder extending out past the participant's thumb, to act as a "sixth finger". A Bumblebee®2 stereo camera (Richmond, Canada) was positioned above the participant's hand to track movement in three dimensions. The color of the cots was used to identify the thumb and locate it in three-dimensional space using a combination of custom code and OpenCV. The location of the thumb relative to the sixth finger was used to determine thumb movement.

Next, the neural decoder (i.e. the software) was trained for a given movement by asking the participant to imagine mimicking hand movements cued to him by an animated virtual hand on a computer monitor. The cued movements corresponded to discrete thumb extension, discrete thumb flexion, and rhythmic thumb wiggle. Each movement cue was directly followed by a cue to rest and the duration of the movement and rest cues was randomly selected between 2.5 sec and 4.5 sec. The ordering of the movement cues was randomly shuffled so the participant could not anticipate the next cue. The neural decoders were trained in training blocks, each consisting of multiple repetitions of each desired motion. This full set of data was used as input for training a nonlinear Support Vector Machine (SVM) algorithm, to generate a robust set of decoders. A decoder for each motion (against all other motions and rest) was built using a nonlinear Gaussian radial basis function kernel to process this full set of data and a non-smooth SVM algorithm that uses sparsity optimization to improve performance.

During the test period, all decoders ran simultaneously and the decoder with the highest output score above zero was used to drive electrical stimulation. The output score of each movement decoder is between −1 and +1. When the output score of a movement decoder exceeded zero, the system enabled stimulation for that movement. If the output scores of multiple movement decoders exceeded zero simultaneously, then the system enabled the movement with the highest decoder score.

Neuromuscular electrical stimulation (NMES) was provided through the use of a custom-made high-definition sleeve. Briefly, the desired movement was evoked by the stimulator providing electrical stimulation through the electrodes on a sleeve wrapped around the participant's forearm. The sleeve contains 130 electrodes and hydrogel disks of 12 mm diameter. The center-to-center spacing of the electrodes is 22 mm along the long axis of the forearm and 15 mm in the transverse direction. Electrical stimulation was provided in the form of current-controlled, monophasic rectangular pulses of 50 Hz pulse rate and 500 µs pulse width. For each movement, a stimulator calibration was performed to determine the appropriate spatial electrode pattern by using a trial-and-error method.

Experiments and Results

Decoded cortical signals were then used to drive the virtual CPG oscillator which in turn controlled the NMES to stimulate the paralyzed muscles and generate movements, thereby bypassing the injured spinal cord. Motor cortical neural activity was continuously recorded as the participant was cued to imagine one of the three trained movements (discrete thumb flexion, discrete thumb extension, and rhythmic thumb wiggle) interleaved with rest periods. Cues were delivered by an animated virtual hand on the computer monitor.

Figures 22A, 22B, 22C:
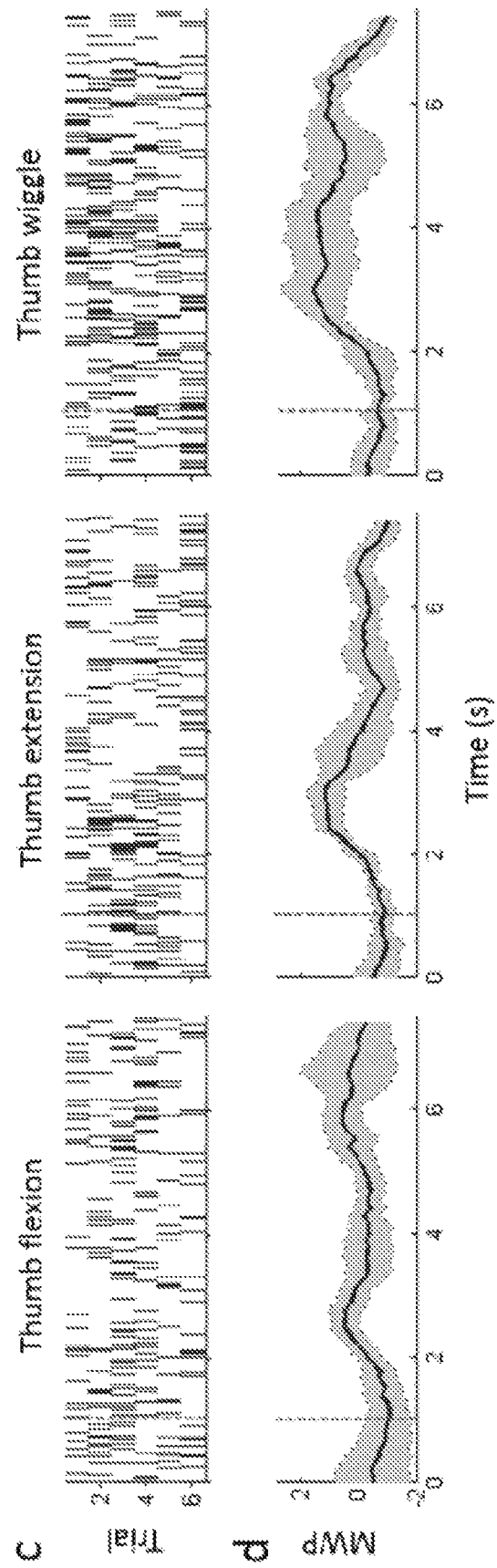
FIGS. 22A-22C are sets of graphs. In each figure, the top graph is a raster histogram from one discriminated unit (channel 7 unit 1) showing the response to attempted thumb movement. Six trials are shown, and each dot in the raster represents a spike. The bottom graph is wavelet processed neural data from channel 7 showing the mean wavelet power (MWP) (dark line), with a confidence interval of ±1 standard deviation around the mean.

FIGS. 22A-22C show the raster histograms from one discriminated unit (channel 7 unit 1) with response to attempted thumb movements and the corresponding wavelet processed neural data showing average mean wavelet power (MWP).

Figure 23A:
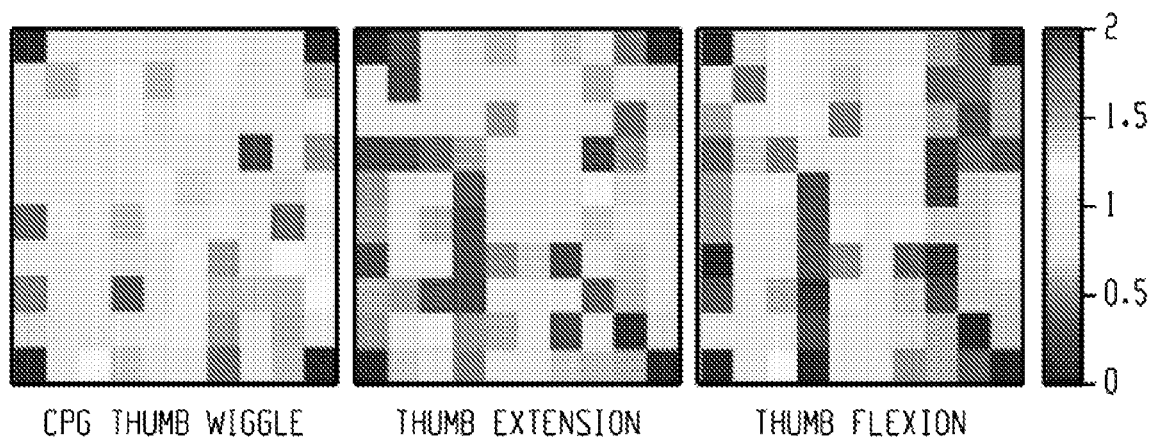
FIG. 23A shows the average normalized mean wavelet power for each electrode in the 96-electrode array for the three different movements. The power is in units of standard deviations away from a baseline non-movement period of rest.
Figure 23B:
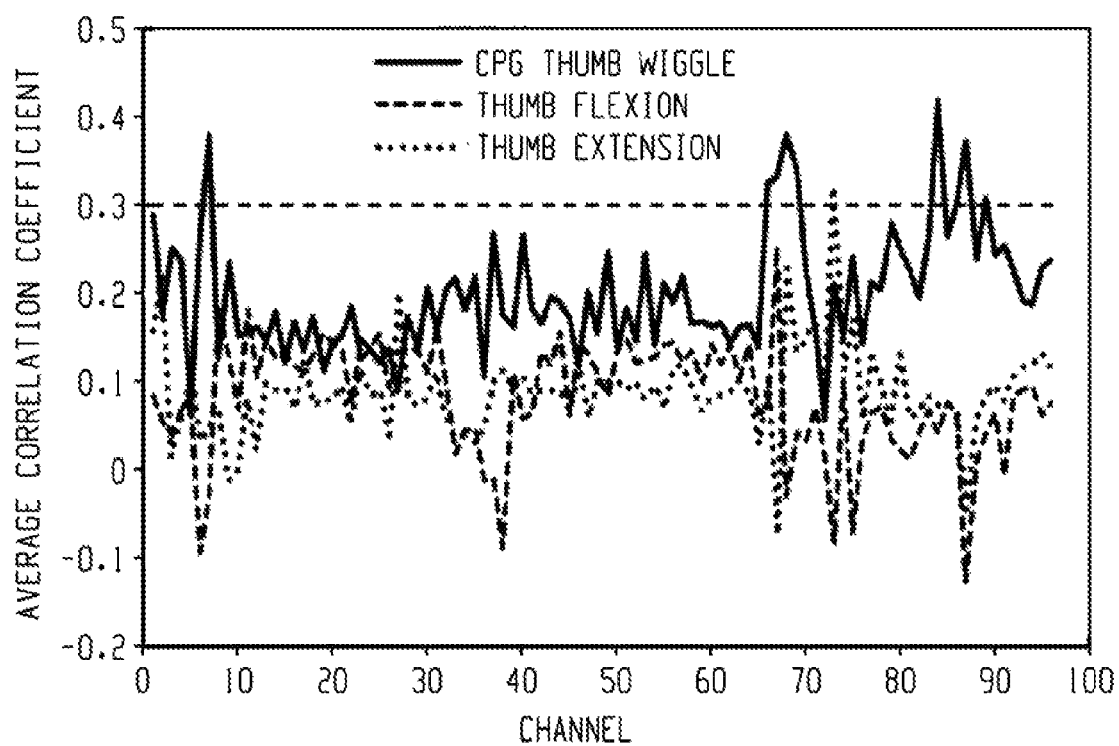
FIG. 23B is a graph showing the average correlation coefficient between the neural activity and the cue vector for each channel, and shows the change in modulation levels on certain channels between the three movements.
Figure 23C:
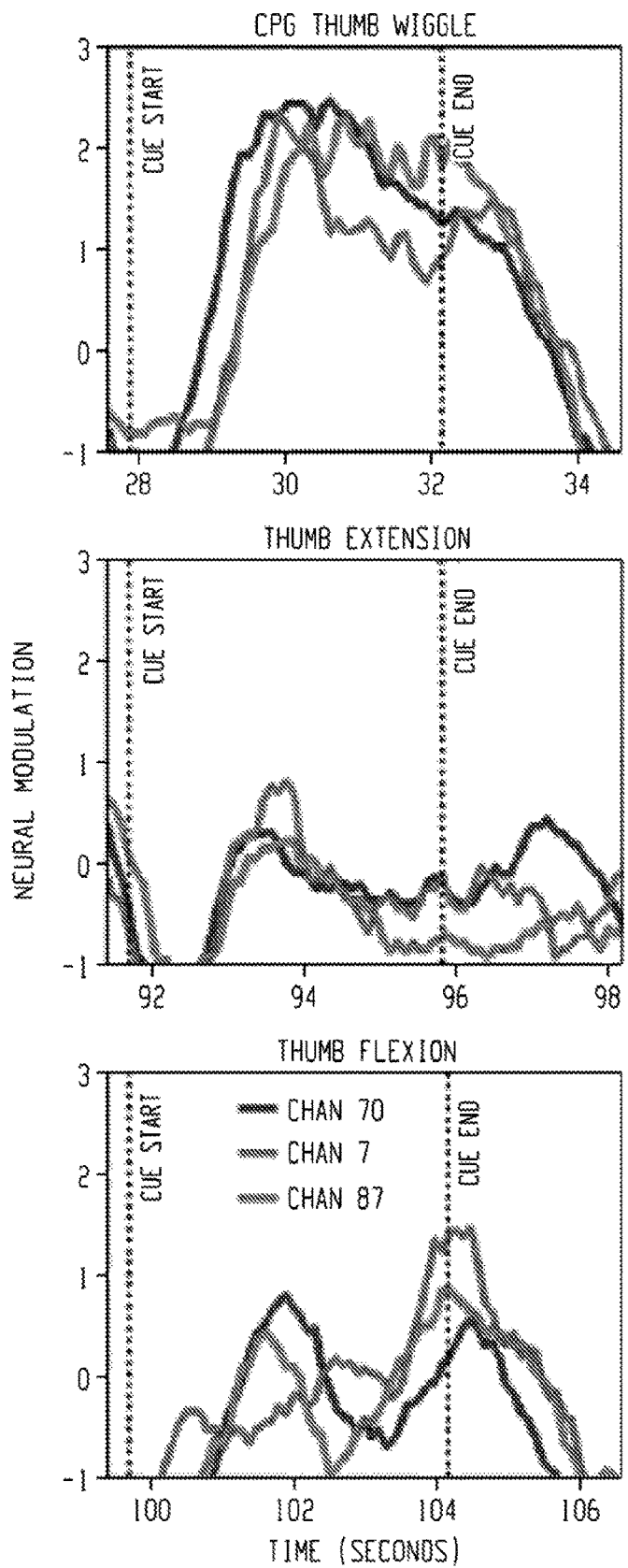
FIG. 23C is a set of graphs showing that channels 7, 70, and 87 show distinct differences in neural modulation when comparing thumb wiggle to chumb flexion and extension. The x-axis is the time in seconds when a cue was given to imagine the noted movement, and the y-axis is the modulation in standard deviations away from the baseline.

FIG. 23A shows representative heat maps of the spatial distribution of the neural activity for the three imagined movements as represented by the normalized MWP overlaid on the physical layout of the array. FIG. 23B shows the correlation coefficient between the cue and the MWP on each channel for each motion (FIG. 3b). The correlation was significantly different (p<0.05) on 79 out of 96 channels when the participant imagined the rhythmic thumb wiggle compared to when he imagined thumb flexion and on 62 out of 96 channels for imagined rhythmic thumb wiggle compared to imagined thumb extension. The MWP on some channels was not only highly correlated (correlation coefficient>0.3) for rhythmic movement, but was also negatively correlated with either the discrete flexion or extension movement. FIG. 23C shows the modulation in MWP on representative channel #7, 70 and 87 for the three imagined movements, showing distinct modulation for imagined thumb wiggle compared to imagined thumb extension and flexion.

Next, to investigate if the cortically-controlled NMES system could differentially control both discrete flexion/extension movements and more complex, rhythmic digit movements, the system's ability to evoke these movements on cue was tested. Test blocks were performed consisting of six trials of each of the three trained movements presented in random order with a rest period between each movement. Cortical activity was continuously decoded using the trained decoders as the participant attempted either the cued movement or rest, as described above. Neural decoder output corresponding to the rhythmic thumb wiggle was used to trigger the virtual CPG oscillator, which used the identified parameters to generate the oscillatory output used by the NMES for real-time stimulation of alternating extensor and flexor muscles in the participant's forearm resulting in a rhythmic thumb wiggle. Neural decoder output classified as either a discrete flexion or discrete extension was fed to the NMES for realtime stimulation of muscles controlling either thumb flexion or extension respectively.

Figures 24A, 24B, 24C:
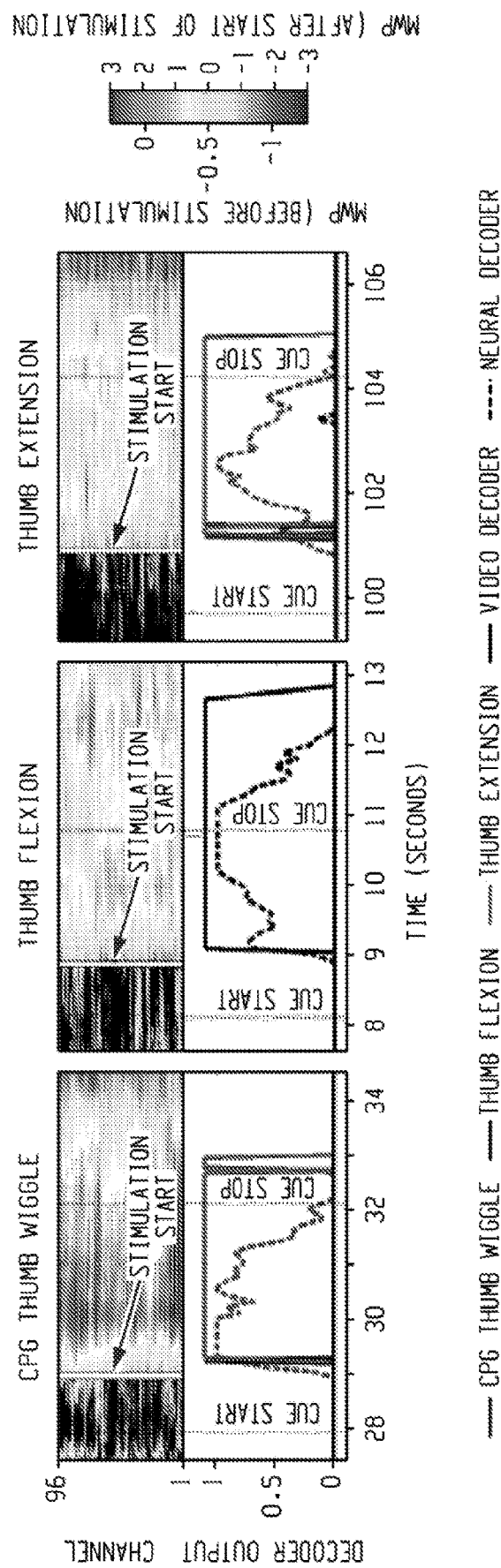
FIGS. 24A-24C are sets of graphs. In each figure, the top graph is a heat map of the mean wavelet power (MWP) before stimulation and after stimulation. The y-axis is the channel, and the x-axis is the time (secs) when the signal is detected. The white line marks when the stimulation is turned on. The MWP is in units of standard deviation away from a baseline non-movement period. In the bottom graph, the dotted line is the neural decoder output score, and the solid line is the physical thumb movement. Only decoder outputs greater than zero are shown for clarity.

Representative data, including modulation of MWP (before and after stimulation begins), decoder outputs, and corresponding movement state are shown in FIG. 24A for thumb wiggle, in FIG. 24B for thumb flexion, and FIG. 24C for thumb extension. MWP increases after stimulation begins due to residual stimulation artifact. However, since the neural decoders were trained with MWP data from before and during stimulation, the neural decoders were not only able to recognize the correct imagined movement to initiate stimulation but also the participant's desire to sustain and subsequently terminate the target movement. The participant was able to successfully initiate, sustain, and complete distinct flexion, extension and wiggle movements through his thoughts alone.

Accuracy was measured by an automated computer-based evaluation of video frames of thumb movements as the fraction of frames that matched the cued movement. Sensitivity was defined as the proportion of movement cues that were identified correctly, and specificity was defined as the proportion of rest cues that were identified correctly. The results obtained are laid out in the table below:

| Movement | Thumb Wiggle | Thumb Extension | Thumb Flexion |
|---|---|---|---|
| Accuracy | 91.5 ± 0.6% | 90.9 ± 0.6% | 84.6 ± 0.8% |
| Sensitivity | 96.4 ± 1.0% | 62.1 ± 2.6% | 94.0 ± 1.3% |
| Specificity | 90.6 ± 0.7% | 96.4 ± 0.4% | 82.9 ± 0.8% |

Using the system, the participant achieved an overall accuracy of 77.4%±0.9% (mean s.d., p<0.01) across all states of rest, wiggle, extension and flexion. The overall accuracy is lower than the individual accuracies because it accumulates the errors for each of the three individual movements.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of creating a neural bridge, comprising:
   (i) measuring a first neural activity of a user;
   (ii) extracting at least one feature from the first measurement of neural activity, and determining a desired movement of a target and a level of movement effort by the user based on the at least one feature;
   (iii) forming an electrical signal to be delivered to the target using both the determined desired movement and the determined level of movement effort by the user and delivering the electrical signal to the target to start movement of the target; and
   (iv) based on a second measurement of neural activity of the user or based on the movement of the target, maintaining or changing the electrical signal being delivered to the target as the target moves, so that the desired movement is achieved.

2. The method of claim 1, further comprising removing at least one artifact from the measurement of neural activity prior to determining the desired movement of the target.

3. The method of claim 1, wherein the at least one extracted feature is a signal amplitude, an amplitude of the signal in a given frequency range, an amplitude of the signal in a wavelet scale, or a firing rate.

4. The method of claim 1, wherein the determining of the desired movement further comprises providing the at least one extracted feature to a non-linear decoder.

5. The method of claim 1, wherein the determining of the desired movement further comprises feeding the at least one extracted feature to a decoder to identify whether a particular movement is desired.

6. The method of claim 1, wherein the determining of the desired movement and the level of movement effort by the user comprises:
   sending the at least one feature to both a discrete multiclass decoder and a movement effort decoder, wherein the discrete multiclass decoder determines the desired movement and the movement effort decoder determines the level of movement effort by the user.

7. The method of claim 6, wherein the outputs from the discrete multiclass decoder and the movement effort decoder are nonlinearly modified to determine the signal delivered to the target.

8. The method of claim 1, wherein the subsequent neural activity or the motion of the target is used to determine a body state of the target, and the signal is dynamically changed based on the determined body state.

9. The method of claim 8, wherein sensor input from the target is used to determine the body state of the target.

10. The method of claim 8, wherein a history of feedback provided to the user is also used to determine the body state of the target.

11. The method of claim 8, wherein a user activation profile is also used to determine the signal sent to the target.

12. The method of claim 1, wherein the signal delivered to the target is a multiplexed signal that includes multiple interleaved signals that do not interfere with each other.

13. The method of claim 1, wherein the target is a body limb or a prosthetic limb, a wheelchair, a cursor on a computer, an exoskeleton, a remote control device, or an external robotic arm.

14. The method of claim 1, wherein the electrical signal sent to the target is determined by identifying actions about multiple joints of the target that will result in the desired movement, and identifying actuating signals to the multiple joints that do not interfere with each other and that will result in the desired movement; and
  wherein the electrical signal delivered to the target is a multiplexed signal containing the multiple actuating signals interleaved together.

15. The method of claim 1, wherein steps (i)-(iv) are repeated continuously.

16. A method of creating a neural bridge, comprising:
  (i) measuring a first neural activity of a user;
  (ii) based on the first measurement of neural activity, determining a desired movement of a target, wherein the determining of the desired movement comprises extracting at least one feature from the measured neural activity by:
    applying a wavelet decomposition to the measured neural activity;
    using at least two scales to approximate power across multiple scales;
    determining a mean of wavelet coefficients for each scale of each channel of the measured neural activity in a small time window;
    calculating a running mean of each scale of each channel of the measured neural activity using a large sliding time window; and
    subtracting the running mean from the mean of wavelet coefficients in the small time window to obtain the at least one feature;
  (iii) delivering an electrical signal to the target to start movement of the target; and
  (iv) based on a second measurement of neural activity of the user or based on the movement of the target, maintaining or changing the electrical signal being delivered to the target as the target moves, so that the desired movement is achieved.

17. An artificial neurostimulation system for providing volitional control of a target by a user, the system comprising:
  at least one set of electrodes configured to measure neural activity of a brain of the user;
  a target configured to receive an electrical signal; and
  an electronic data processing device programmed to perform operations including:
    determining a desired rhythmic movement of the target that is coordinated by a Central Pattern Generator (CPG) neural network based on a first measurement of neural activity;
    delivering an electrical signal to the target using a CPG oscillator to start movement of the target; and
    based on a second measurement of neural activity of the brain of the user or based on the movement of the target, maintaining or changing the electrical signal being delivered to the target as the target moves, so that the desired rhythmic movement is achieved.

18. A non-transitory storage medium storing instructions readable and executable by an electronic data processing device to perform a neurostimulation method comprising:
  determining a desired movement of the target based on a first measurement of neural activity of a brain of a user including determining whether the desired movement is a discrete movement or a rhythmic movement coordinated by a Central Pattern Generator (CPG) neural network;
  delivering an electrical signal to the target to start movement of the target including, for a rhythmic movement, delivering the electrical signal to the target using a CPG oscillator; and
  based on a second measurement of neural activity of the brain of the user or based on the movement of the target, maintaining or changing the electrical signal being delivered to the target as the target moves, so that the desired movement is achieved.

19. An electronic data processing device programmed to perform operations comprising:
  determining a desired movement of a limb of a user, wherein the limb comprises a hand, based on a first measurement of neural activity of the brain of the user;
  delivering an electrical signal to the limb to start movement of the limb and measuring a second neural activity of the brain of the user; and
  based on the second neural activity of the user or based on the movement of the limb, maintaining or changing the electrical signal being delivered to the limb as the limb moves, so that the desired movement of the limb is achieved.

* * * * *